US009063155B2

(12) United States Patent
Brown

(10) Patent No.: US 9,063,155 B2
(45) Date of Patent: Jun. 23, 2015

(54) IMMUNOTHERAPEUTIC METHOD OF TREATING NEOPLASTIC CONDITIONS

(75) Inventor: Michael Paul Brown, St. Georges (AU)

(73) Assignee: Medvet Science Pty Ltd, Stepney (AU)

( * ) Notice: Subject to any disclaimer, the term of this patent is extended or adjusted under 35 U.S.C. 154(b) by 738 days.

(21) Appl. No.: 10/546,552

(22) PCT Filed: Feb. 23, 2004

(86) PCT No.: PCT/AU2004/000223
§ 371 (c)(1),
(2), (4) Date: Oct. 16, 2006

(87) PCT Pub. No.: WO2004/073739
PCT Pub. Date: Sep. 2, 2004

(65) Prior Publication Data
US 2007/0042432 A1 Feb. 22, 2007

(30) Foreign Application Priority Data

Feb. 21, 2003 (AU) .............................. 2003900777
Mar. 6, 2003 (AU) .............................. 2003901126

(51) Int. Cl.
A61K 39/395 (2006.01)
G01N 33/68 (2006.01)
A61K 47/48 (2006.01)
A61K 51/10 (2006.01)
C07K 16/18 (2006.01)
G01N 33/50 (2006.01)
C07K 16/28 (2006.01)

(52) U.S. Cl.
CPC ...... G01N 33/6875 (2013.01); A61K 47/48538 (2013.01); A61K 51/1018 (2013.01); C07K 16/18 (2013.01); G01N 33/5017 (2013.01); G01N 2510/00 (2013.01)

(58) Field of Classification Search
None
See application file for complete search history.

(56) References Cited

FOREIGN PATENT DOCUMENTS

WO 99/53757 10/1999
WO 2004/003554 1/2004

OTHER PUBLICATIONS

Al-Ejeh et al., Chemotherapy synergizes with radioimmunotherapy targeting La autoantigen in tumors, 2009a, PLoS One, vol. 4, issue 2, e4630, pp. 1-13.*
Al-Ejeh et al., APOMAB, a La-Specific monoclonal antibody, detects the apoptotic tumor response to life-prolonging and DNA-Damaging chemotherapy, 2009b, PLoS One, vol. 4, issue 2, e4558, pp. 1-11.*

Bachmann, M. et al., "Association of La and Ro antigens with intracellular structures in HEp-2 carcinoma cells," Cell Biology 83:7770-7774, Oct. 1986.
Casciola-Rosen, L. et al., "Autoantigens Targeted in Systemic Lupus Erythematosus Are Clustered in Two Populations of Surface Structures on Apoptotic Keratinocytes," J. Exp. Med. vol. 179:1317-1330, Apr. 1994.
Friedman, D. et al., "Congenital Heart Block in Neonatal Lupus: The Pediatric Cardiologist's Perspective," Indian Journal of Pediatrics 69:517-522, Jun. 2002.
Kondo, Y. et al., "Treatment of prostate cancer in vitro and in vivo with 2-5A-anti-telomerase RNA component," Oncogene vol. 19:2205-2211, 2000.
Lawley, W. et al., "Rapid lupus autoantigen relocalization and reactive oxygen species accumulation following ultraviolet irradiation of human keratinocytes," Rheumatology 39(3):253-261, Mar. 2000.
McArthur, C. et al., "Intracellular trafficking and surface expression of SS-A (RO), SS-B (La), poly(ADP-ribose) polymerase and α-fodrin autoantigens during apoptosis in human salivary gland cells induced by tumour necrosis factor- α," Archives of Oral Biology vol. 47:443-448, 2002.
Meyer, O., "Actualités sur les anti-SSA/Ro et anti-SSB/La," Ann. Med. Interne. 153(8):520-529, Dec. 2002. (Abstract).
Miranda, M.-E. et al., "Accessibility of SSA/Ro and SSB/La Antigens to Maternal Autoantibodies in Apoptotic Human Fetal Cardiac Myocytes," Journal of Immunology 161(9):5061-5069, Nov. 1, 1998.
Miranda-Carus, M.-E. et al., "Anti-SSA/Ro and Anti-SSB/La Autoantibodies Bind the Surface of Apoptotic Fetal Cardiocytes and Promote Secretion of TNF-α by Macrophages," Journal of Immunology 165(9):5345-5351, Nov. 1, 2000.
Miranda-Carus, M.-E. et al., "Translocation of SSA/Ro and SSB/La in apoptotic human fetal cardiocytes: Pathogenic role in CHB," Journal of Investigative Medicine 46(3):227A, Mar. 1998. (Abstract).
Ohlsson, M. et al., "Subcellular Redistribution and Surface Exposure of the Ro52, Ro60 and La48 Autoantigens During Apoptosis in Human Ductal Epithelial Cells: a Possible Mechanism in the Pathogenesis of Sjogren's Syndrome," Scand. J. Immunol. 56:456-469, Nov. 5, 2002.

(Continued)

Primary Examiner — Christine J Saoud
(74) Attorney, Agent, or Firm — Seed IP Law Group PLLC

(57) ABSTRACT

The present invention relates generally to a method for detecting an aberrant cell, and more particularly an apoptotic cell, in a subject or in a biological sample from said subject, and agents useful for same. The presence of the aberrant cell or group of aberrant cells provides an indication of a particular disease or condition or a propensity for development of a disease or condition. More particularly, the present invention contemplates a method for detecting an apoptotic cell by detecting the presence of extranuclear nuclear molecules, in particular La, or a relative increase in extranuclear nuclear molecule levels. The present invention further provides a method for diagnosing or monitoring conditions characterized by aberrant, unwanted or otherwise inappropriate cellular apoptosis in a subject or in a biological sample from said subject by screening for up-regulation of extranuclear nuclear molecule levels in a cell or group of cells. The present invention provides diagnostic agents useful for detecting these molecules. Such diagnostic agents include immunointeractive molecules, such as antibodies.

16 Claims, 18 Drawing Sheets

(56) References Cited

OTHER PUBLICATIONS

Tran, H. et al., "Subcellular Redistribution of La/SSB Autoantigen During Physiologic Apoptosis in the Fetal Mouse Heart and Conduction System," *Arthritis & Rheumatism* vol. 46(1):202-208, Jan. 2002.

Wu, X. et al., "Secondary Necrosis Is a Source of Proteolytically Modified Forms of Specific Intracellular Autoantigens," *Arthritis & Rheumatism* vol. 44(11):2642-2652, Nov. 2001.

Yang, Y.-S. et al., "Autoantigen Ro52 directly interacts with human IgG heavy chain in vivo in mammalian cells," *Molecular Immunology* 37:591-602, Aug. 18, 2000.

Ayukawa et al., "La Autoantigen Is Cleaved in the COOH Terminus and Loses the Nuclear Localization Signal during Apoptosis," The Journal of Biological Chemistry 275(44): 34465-34470, Nov. 3, 2000.

Bruns et al., "Therapy of Human Pancreatic Carcinoma Implants by Irinotecan and the Oral Immunomodulator JBT 3002 Is Associated with Enhanced Expression of Inducible Nitric Oxide Synthase in Tumor-infiltrating Macrophages," Cancer Research 60: 2-7, Jan. 1, 2000.

Goldenberg, "New developments in monoclonal antibodies for cancer detection and therapy," CA: A Cancer Journal for Clinicians 44(1): 43-64, Jan./Feb. 1994.

Kowalczyk et al., "Cancer immunotherapy using cells modified with cytokine genes," Acta Biochimica Polonica 50 (3): 613-624, 2003.

Rosenblatt et al., "Potential Role of Chemokines in Immune Therapy of Cancer," IMAJ 4: 1054-1059, Nov. 2002.

Dahle et al., "Targeted cancer therapy with a novel low-dose rate α-emitting radioimmunoconjugate," *Blood* 110(6): 2049-2056, Sep. 15, 2007.

Kovtun et al., "Antibody-Drug Conjugates Designed to Eradicate Tumors with Homogeneous and Heterogeneous Expression of the Target Antigen," *Cancer Res* 66(6): 3214-3221, Mar. 15, 2006.

Liersch et al., "Phase II Trial of Carcinoembryonic Antigen Radioimmunotherapy with $^{131}$I-Labetuzumab After Salvage Resection of Colorectal Metastases in the Liver: Five-Year Safety and Efficacy Results," *J Clin Oncol* 23(27): 6763-6770, Sep. 20, 2005.

Morschhauser et al., "Efficacy and safety of yttrium-90 ibritumomab tiuxetan in patients with relapsed or refractory diffuse large B-cell lymphoma not appropriate for autologous stem-cell transplantation," *Blood* 110(1): 54-58, Jul. 1, 2007.

Cheson, "Radioimmunotherapy of non-Hodgkin Lymphomas," *Blood* 101(2):391-398, Jan. 15, 2003.

\* cited by examiner

US 9,063,155 B2

IMMUNOTHERAPEUTIC METHOD OF TREATING NEOPLASTIC CONDITIONS

FIELD OF THE INVENTION

The present invention relates generally to a method for detecting an aberrant cell, and more particularly an apoptotic cell, in a subject or in a biological sample from said subject, and agents useful for same. The presence of the aberrant cell or group of aberrant cells provides an indication of a particular disease or condition or a propensity for development of a disease or condition. More particularly, the present invention contemplates a method for detecting an apoptotic cell by detecting the presence of extranuclear nuclear molecules, in particular La, or a relative increase in extranuclear nuclear molecule levels. The present invention further provides a method for diagnosing or monitoring conditions characterised by aberrant, unwanted or otherwise inappropriate cellular apoptosis in a subject or in a biological sample from said subject by screening for up-regulation of extranuclear nuclear molecule levels in a cell or group of cells. The present invention provides diagnostic agents useful for detecting these molecules. Such diagnostic agents include immunointeractive molecules, such as antibodies.

The present invention still further relates to a means for therapeutic targeting either in vitro or in vivo. The present invention still further provides antibodies and, in particular, monoclonal antibodies, which interact specifically with epitopes present on the subject molecule. The ability to target apoptotic cells may be useful, inter alia, in a range of diagnostic, immuno-therapeutic and immuno-prophylactic treatments characterised by the presence of apoptotic cells.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Malignant tumours, or cancers, grow in an uncontrolled manner, invade normal tissues, and often metastasize and grow at sites distant from the tissue of origin. In general, cancers are derived from one or only a few normal cells that have undergone a poorly understood process called malignant transformation. Cancers can arise from almost any tissue in the body. Those derived from epithelial cells, called carcinomas, are the most common kinds of cancers. Sarcomas are malignant tumours of mesenchymal tissues, arising from cells such as fibroblasts, muscle cells, and fat cells. Solid malignant tumours of lymphoid tissues are called lymphomas, and marrow and blood-borne malignant tumours of lymphocytes and other hematopoietic cells are called leukemias.

Cancer is one of the three leading causes of death in industrialized nations. As treatments for infectious diseases and the prevention of cardiovascular disease continues to improve, and the average life expectancy increases, cancer is likely to become the most common fatal disease in these countries. Therefore, successfully treating cancer requires that all the malignant cells be removed or destroyed without killing the patient. An ideal way to achieve this would be to induce an immune response against the tumour that would discriminate between the cells of the tumour and their normal cellular counterparts. However, immunological approaches to the treatment of cancer have been attempted for over a century with unsustainable results.

Accordingly, current methods of treating cancer continue to follow the long used protocol of surgical excision (if possible) followed by radiotherapy and/or chemotherapy, if necessary. The success rate of this rather crude form of treatment is extremely variable but generally decreases significantly as the tumour becomes more advanced and metastasises. Further, these treatments are associated with severe side effects including disfigurement and scarring from surgery (e.g. mastectomy or limb amputation), severe nausea and vomiting, chemotherapy, and most significantly, the damage to normal tissues such as the hair follicles, gut and bone marrow which is induced as a result of the relatively non-specific targeting mechanism of the toxic drugs which form part of most cancer treatments.

Further, most anti-cancer treatments, which include cytotoxic chemotherapeutic agents, signal transduction inhibitors, radiotherapy, monoclonal antibodies and cytotoxic lymphocytes, kill cancer cells by apoptosis. Although tumours may contain a proportion of apoptotic cells and even areas of necrosis before anti-cancer treatment is given, an increased number of apoptotic cells and larger areas of necrosis are anticipated in tumours that respond to the anti-cancer treatment. However, when cytotoxic chemotherapeutic agents are used for the treatment of advanced cancer, the degree of cell kill and thus the response of the tumour to the first treatment is frequently difficult to assess. Conventionally, patients receive a minimum of three cycles of chemotherapy before a clinical and radiological assessment of tumour response is made. Usually, only a minority of patients with advanced cancer responds to cytotoxic drugs and so patients may experience the side effects of treatment without obtaining benefit. Hence, there is an unmet medical need for a diagnostic method that would enable rapid, convenient and reliable detection of tumour cell kill after the first cycle of treatment that would predict treatment response, which in turn often predicts survival. For example, the use of positron emission tomography with fluoro-deoxyglucose (FDG-PET) in patients with oesophageal adenocarcinoma, who received chemoradiotherapy before surgery, differentiated treatment responders from non-responders with >90% sensitivity and specificity and tended to predict those who would subsequently undergo a curative resection of their tumours. Knowing whether the tumour is responding early would spare the majority of patients from ineffective and potentially toxic treatment. Then, non-responding patients can be offered second line treatments or clinical trials of investigational agents.

Accordingly, there is an urgent and ongoing need to develop new methods of diagnosing and treating cancers in a targeted manner. This notion of effective targeted killing of malignant cells has been, to date, unattainable.

In work leading up to the present invention, it has been surprisingly determined that nuclear molecules can in fact be reliably and detectably screened for, utilising an interactive molecule, such as an immunointeractive molecule, and further, provides an accurate and reliable means of detecting apoptotic cells in a highly specific manner either in vitro or in vivo. In particular, the diagnosis and monitoring of tumours and metastases, which are often characterised by the presence of a proportion of apoptotic cells, has now been facilitated. Still further, the use of the interactive molecules of the present invention has now been determined to facilitate anti-tumour therapy in a highly targeted and specific context.

SUMMARY OF THE INVENTION

One aspect of the present invention contemplates a method for detecting an apoptotic cell in a subject or in a biological sample from said subject, said method comprising contacting cells or cell extracts from said subject or said biological sample with an interactive molecule directed to a nuclear molecule or antigenic portion thereof and screening for the interactive molecule-nuclear molecule complex formation wherein the non-nuclear localisation of said complex is indicative of an apoptotic cell.

Another aspect of the present invention contemplates a method for detecting an apoptotic cell in a subject or in a biological sample from said subject, said method comprising contacting cells or cell extracts from said subject or said biological sample with an immunointeractive molecule directed to a nuclear molecule or antigenic portion thereof and screening for immunointeractive molecule-nuclear molecule complex formation wherein the non-nuclear localisation of said complex is indicative of an apoptotic cell.

In yet another aspect there is provided a method for detecting an apoptotic neoplastic cell in a subject or in a biological sample from said subject, said method comprising contacting cells or cell extracts from said subject or said biological sample with an immunointeractive molecule directed to La or antigenic portion thereof and screening for immunointeractive molecule-La complex formation wherein the non-nuclear localisation of said complex is indicative of an apoptotic neoplastic cell.

In still another aspect there is provided a method for detecting an apoptotic neoplastic cell in a subject or in a biological sample from said subject, said method comprising contacting cells or cell extracts from said subject or said biological sample with an antibody directed to La or antigenic portion thereof and screening for antibody-La complex formation wherein the non-nuclear localisation of said complex is indicative of an apoptotic cell.

Another aspect of the present invention is directed to a method for diagnosing or monitoring a condition characterised by aberrant, unwanted or otherwise inappropriate cellular apoptosis in a subject, said method comprising contacting cells or cell extracts from said subject or a biological sample from said subject with a nuclear molecule-binding effective amount of an interactive molecule directed to said nuclear molecule or an antigenic determinant or epitope thereof and quantitatively or qualitatively detecting nuclear molecule-immunointeractive molecule complex formation wherein the non-nuclear localisation of said complex is indicative of cellular apoptosis.

In yet another aspect the present invention is directed to a method for diagnosing or monitoring a neoplastic condition in a subject, said method comprising contacting said cells or cell extracts from said subject or a biological sample from said subject with an La-binding effective amount of an immunointeractive molecule directed to said La or an antigenic determinant or epitope thereof and quantitatively or qualitatively detecting La-immunointeractive molecule complex formation wherein the non-nuclear localisation of said complex is indicative of cellular apoptosis and said cellular apoptosis is indicative of said neoplastic condition.

The present invention further contemplates an assay to detect an apoptotic cell in a biological sample, said assay including the steps of:
(1) contacting an interactive molecule directed to a nuclear molecule or an antigenic determinant thereof with a biological sample suspected of containing said nuclear molecule; and
(2) subjecting the complex formed in step (1) to a signal detection step
wherein detecting non-nuclear interactive molecule-nuclear molecule complex formation is indicative of apoptotic cells.

Another aspect of the present invention contemplates a method for detecting apoptotic cells in a human, said method comprising introducing into said patient an interactive molecule directed to a nuclear molecule or an antigenic determinant thereof labelled with a reporter molecule, allowing dissemination of the labelled interactive molecule throughout the circulatory system, or to selected parts of the circulatory system and then subjecting said patient to reporter molecule-detection means to identify the location of the interactive molecule.

A further aspect of the present invention provides a method of detecting, in a sample, La or fragment, variant or derivative thereof comprising contacting the sample with an antibody or fragment or derivative thereof and detecting the formation of a complex comprising said antibody and La or fragment, variant or derivative thereof wherein non-nuclear localisation of La is indicative of apoptosis.

The present invention still further contemplates the use of an interactive molecule directed to a nuclear molecule in the manufacture of a quantitative or semi-quantitative diagnostic kit to detect apoptotic cells in a biological sample from a patient. The kit may come with instructions for use and may be automated or semi-automated or in a form which is compatible with automated machine or software.

Still yet another aspect of the present invention is directed to a method of therapeutically and/or prophylactically treating a condition in a subject, which condition is characterised by cellular apoptosis, said method comprising administering to said subject an effective amount of an interactive molecule directed to a nuclear molecule or antigenic portion thereof, which interactive molecule is linked, bound or otherwise associated with a therapeutic or prophylactic effector mechanism, for a time and under conditions sufficient to treat said condition.

The present invention more particularly provides a method of therapeutically and/or prophylactically treating a neoplastic condition in a subject, said method comprising administering to said subject an effective amount of an immunointeractive molecule directed to La or antigenic portion thereof, which immunointeractive molecule is linked, bound or otherwise associated with a therapeutic effector mechanism, for a time and under conditions sufficient to inhibit, reduce or otherwise down-regulate the growth of the neoplasm.

In a further aspect there is provided a method of therapeutically treating a metastatic cancer in a subject, said method comprising administering to said subject an effective amount of an immunointeractive molecule directed to La or antigenic portion thereof, which immunointeractive molecule is linked, bound or otherwise associated with a therapeutic effector mechanism, for a time and under conditions sufficient to inhibit, reduce or otherwise down-regulate the growth of said metastatic cancer.

Another aspect of the present invention contemplates the use of an anti-nuclear molecule interactive molecule conjugated to an effector mechanism, in the manufacture of medicament for the treatment of a condition in a subject, which condition is characterised by cellular apoptosis, wherein said effector mechanism treats said condition.

In yet another further aspect, the present invention contemplates a pharmaceutical composition comprising the modulatory agent as hereinbefore defined together with one or more pharmaceutically acceptable carriers and/or diluents. Said agents are referred to as the active ingredients.

Yet another aspect of the present invention relates to the agent as hereinbefore defined, when used in the method of the present invention.

BRIEF DESCRIPTION OF THE DRAWINGS

FIG. 2 is a schematic representation of anti-La functioning. Once anti-La antibodies diagnose chemotherapy-induced apoptosis among cancer cells (FIG. 2A), they may subsequently deliver other modalities of cancer treatment, which have non-cross resistant mechanisms of action, to those viable cancer cells that remain in the vicinity of the dead cells (FIG. 2B).

DETAILED DESCRIPTION OF THE INVENTION

Figure 1:
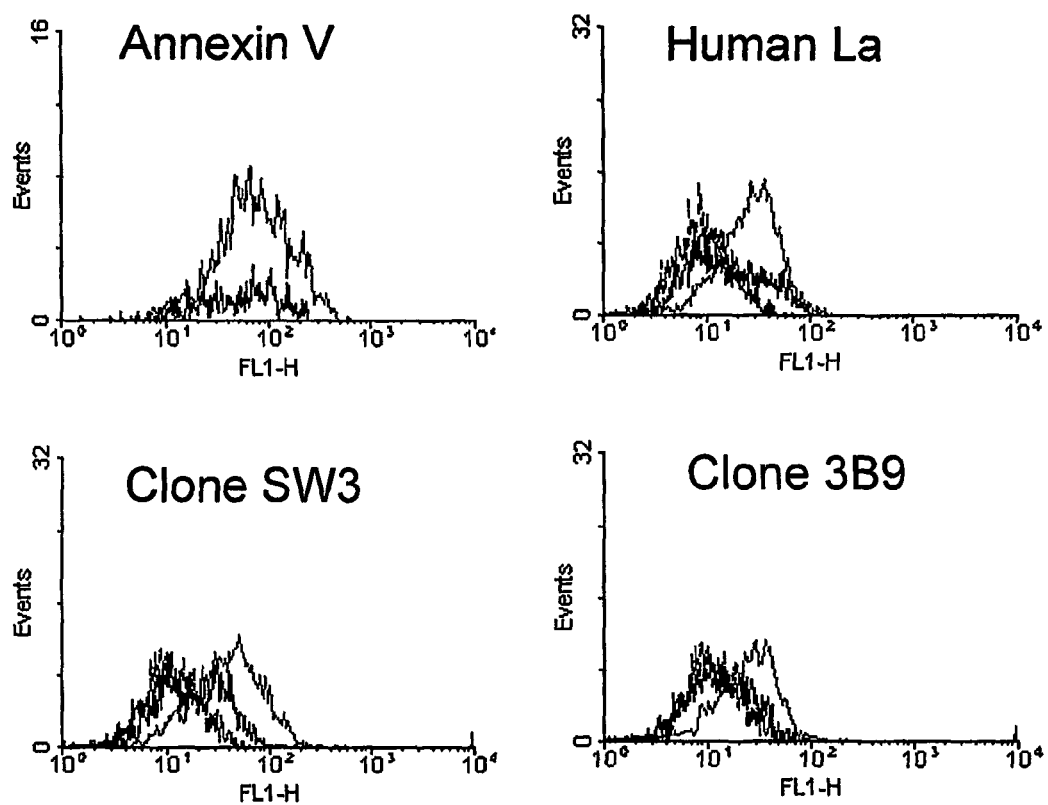
FIG. 1 is a graphical representation of the prostate cancer cell line LNCAP which was cultured with or without serum for 24 hours before the cells were scraped off the tissue culture flask for analysis by flow cytometry. Cells were stained with Propidium Iodide (PI) and (A) Annexin V-FITC, (B) Normal human serum (NHS) or affinity purified human La autoantibodies (hLa) and mouse anti-human IgG-FITC, (C) Murine isotype control or murine anti-hLa mAb clone SW3 and anti-mouse IgG-FITC, (D) Murine isotype control or murine anti-hLa mAb clone 3B9 and anti-mouse IgG-FITC. Histograms are shown for cells that were gated as PI intermediate (i.e. late apoptotic cells). Blue line, NHS or murine isotype control; Black line, Annexin V or anti-La staining for LNCaP cells grown in serum; Red line, Annexin V or anti-La staining for serum-starved LNCaP cells.

The present invention is predicated, in part, on the surprising determination that screening for nuclear molecule expression outside the nucleus utilising an immunointeractive molecule provides a highly specific and reliable means of detecting the presence of apoptotic cells either in vitro or in vivo. This finding is of particular significance since previous experimental work directed to screening for (and thereby identifying) antigens associated with apoptotic cells have not identified nuclear molecules, in particular La, as candidate antigens. Rather, other unrelated antigens such as phosphatidylserine have been repeatedly identified. Unfortunately, these unrelated molecules exhibit significant disadvantages, in particular the fact that transient extracellular expression can occur due to non-apoptotic events, such as mechanical or other disruption of the cell. Still further, previously analysed nuclear molecules such as La have been dismissed as markers of apoptotic cells, per se, on the basis that cellular staining was thought to be the result of an active process, by some apoptotic cells, of internalisation of cell surface complexes of antibody-antigen. That is, membrane permeability as a route of antibody entry to the cell had been dismissed. Accordingly, no means of identifying apoptotic cells, per se, as a class had been developed. However, there has now been developed a method for the in vitro and in vivo detection of late apoptotic cells and apoptotic bodies using anti-nuclear immunointeractive molecules, in particular, anti-La/SS-B immunointeractive molecules. The method is direct and does not require additional steps such as permeabilisation to demonstrate binding, as has been required prior to the advent of the present invention. It had previously been understood that anti-nuclear antibody binding was not related to apoptosis induction, that it depended upon permeabilisation of the cell, that it was surface membrane-related and depended upon mechanisms of binding other than passive entry and specific binding to antigen contained within apoptotic bodies.

The surprising identification of nuclear molecules such as La as highly specific, detectable and exclusive markers of apoptotic cells now permits the development of a range of agents and methods directed to diagnosing and monitoring apoptotic cellular populations and, in particular, tumours and their metastases. Still further, it has been determined that the use of immunointeractive molecules directed to these nuclear molecules provides a highly specific means of targeting therapeutic and/or prophylactic treatments to conditions characterised by the presence of apoptotic cells. Of particular significance in the specific context of tumour therapy has been the finding that targeting of an anti-La immunointeractive molecules, for example, to apoptotic cells within a tumour can be successfully utilised to provide a means for achieving killing of bystander non-apoptotic tumour cells, such as via the delivery of a toxic molecule.

Accordingly, one aspect of the present invention contemplates a method for detecting an apoptotic cell in a subject or in a biological sample from said subject, said method comprising contacting cells or cell extracts from said subject or said biological sample with an interactive molecule directed to a nuclear molecule or antigenic portion thereof and screening for the interactive molecule-nuclear molecule complex formation wherein the non-nuclear localisation of said complex is indicative of an apoptotic cell.

More particularly, the present invention contemplates a method for detecting an apoptotic cell in a subject or in a biological sample from said subject, said method comprising contacting cells or cell extracts from said subject or said biological sample with an immunointeractive molecule directed to a nuclear molecule or antigenic portion thereof and screening for immunointeractive molecule-nuclear molecule complex formation wherein the non-nuclear localisation of said complex is indicative of an apoptotic cell.

Reference to a "nuclear molecule" should be understood as a reference to any proteinaceous or non-proteinaceous molecule which is either permanently or transiently present prior to apoptosis, in the nucleus of the cell which becomes the subject of apoptosis. Preferably, said nuclear molecule is Ro52, Ro60, La/SS-B, gelsolin, α-fodrin, fibrillarin, U1 small nuclear ribonuclear protein (U1 snRNP), heteronuclear ribonucleoproteins (hnRNP), lamin B, Poly(ADP-Ribose) Polymerase (PARP), Proliferating Cell Nuclear Antigen (PCNA), SC-35 splicing factor, Smith (Sm) antigen. Even more preferably said nuclear molecule is La.

Without limiting the present invention in any way, anti-La antibodies specifically detect apoptosis. Prior understanding of the non-nuclear localisation of La and its subsequent detection on the exterior surface of apoptotic blebs was held to be dependent upon caspase activation, which is a specific outcome of apoptosis. However, although caspase activity is not detected in late apoptotic cells (P. Smolewski et al. *IJ Immunol Methods* 2002) it has been determined that nuclear molecules such as La can still be detected. Late apoptotic cells are not detected readily by other diagnostic methods.

Reference to "non-nuclear localisation" should be understood as a reference to the subject nuclear molecule being localised to any region of the cell, or part thereof, other than within the intact nucleus. Preferably, the subject non-nuclear localisation is such that the La is exposed to the extracellular environment, herein referred to as "extracellular localisation", as occurs, for example, where the nuclear molecule is translocated to the cytoplasm of an apoptotic cell, the membrane of which cell has become permeable or where the molecule is expressed within an apoptotic body, which bodies form within the apoptosing cell and are ultimately released to the extracellular environment upon complete disintegration of the apoptosing cell.

Reference to an "apoptotic" cell should be understood as a reference to a cell which is undergoing, or has undergone, apoptosis. Without limiting the present invention to any one theory or mode of action, apoptosis is an active process requiring metabolic activity by the dying cell. Apoptosis is often characterised by shrinkage of the cell, cleavage of the DNA into fragments (which give a "laddering pattern" on gels) and by condensation and margination of chromatin. Cellular apoptosis occurs in a wide variety of contexts. Accordingly, identification of the non-nuclear localisation of La, for example, together with the nature and location of the cell type expressing this molecule provides a means of monitoring and/or diagnosing a wide variety of conditions including infarction of cardiac muscle (heart attack) or brain (stroke), or autoimmune and other inflammatory diseases, or viral diseases such as AIDS, or neurogenerative diseases such as Alzheimer's disease or Parkinson's disease, or acute solid organ or bone marrow transplant rejection, or chemotherapy- or radiation-induced tissue damage ('mucositis') or a neoplasm. In one preferred embodiment, the subject apoptotic cell is an apoptotic neoplastic cell.

According to this preferred embodiment, there is provided a method for detecting an apoptotic neoplastic cell in a subject or in a biological sample from said subject, said method comprising contacting cells or cell extracts from said subject or said biological sample with an immunointeractive molecule directed to La or antigenic portion thereof and screening for immunointeractive molecule-La complex formation wherein the non-nuclear localisation of said complex is indicative of an apoptotic neoplastic cell.

Preferably, said non-nuclear localisation occurs within the cytoplasm of the apoptotic cell or within the apoptotic bodies formed by the apoptotic cell.

Reference to a "neoplastic cell" should be understood as a reference to a cell exhibiting abnormal growth. The term "growth" should be understood in its broadest sense and includes reference to proliferation. In this regard, an example of abnormal cell growth is the uncontrolled proliferation of a cell. The neoplastic cell may be a benign cell or a malignant cell. The subject neoplastic cell may be any cell type such as an epithelial cell or a non-epithelial cell.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms "neoplasia" and "hyperplasia" can be used interchangeably, referring generally to cells experiencing abnormal cell growth rates. Neoplasias and hyperplasias include "tumours" which may be either benign, pre-malignant or malignant. The term "neoplasm" should be understood as a reference to a lesion, tumour or other encapsulated or unencapsulated mass or other form of growth which comprises neoplastic cells.

As used herein, the terms "hyperproliferative" and "neoplastic" are used interchangeably and refer to those cells in an abnormal state or condition characterized by rapid proliferation or neoplasm. The terms are meant to include all types of cancerous growths or oncogenic processes, metastatic tissues or malignantly transformed cells, tissues or organs irrespective of histopathologic type or state of invasiveness. "Pathologic hyperproliferative" cells occur in disease states characterized by malignant tumour growth.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostate carcinomas, endocrine system carcinomas and melanomas. Exemplary carcinomas include those forming from tissue of the breast. The term also includes carcinosarcomas, e.g. which include malignant tumours composed of carcinomatous and sarcomatous tissues. An "adenocarcinoma" refers to a carcinoma derived from glandular tissue or in which the tumour cells form recognizable glandular structures.

The term "neoplasm" as used herein encompasses all the terms discussed in the preceding three paragraphs.

Examples of neoplasms and neoplastic cells encompassed by the present invention include, but are not limited central nervous system tumours, retinoblastoma, neuroblastoma and other paediatric tumours, head and neck cancers (e.g. squamous cell cancers), breast and prostate cancers, lung cancer (both small and non-small cell lung cancer), kidney cancers (e.g. renal cell adenocarcinoma), oesophagogastric cancers, hepatocellular carcinoma, pancreaticobiliary neoplasias (e.g. adenocarcinomas and islet cell tumours), colorectal cancer, cervical and anal cancers, uterine and other reproductive tract cancers, urinary tract cancers (e.g. of ureter and bladder), germ cell tumours (e.g. testicular germ cell tumours or ovarian germ cell tumours), ovarian cancer (e.g. ovarian epithelial cancers), carcinomas of unknown primary, human immunodeficiency associated malignancies (e.g. Kaposi's sarcoma), lymphomas, leukemias, malignant melanomas, sarcomas, endocrine tumours (e.g. of thyroid gland), mesothelioma and other pleural tumours, neuroendocrine tumours and carcinoid tumours.

Reference herein to "La" includes reference to all forms of La or their homologues, or orthologs or derivatives. Reference to "La" should be understood to include reference to any isoforms which arise from alternative splicing of La mRNA or mutants or polymorphic variants of La. It should also be understood that "La" is a molecule which is alternatively term SS-B.

The "interactive molecule" is any molecule having specificity (not necessarily exclusive specificity, although this is preferable) and binding affinity for La or its antigenic parts or its homologues or derivatives. Examples of interactive molecules include immunointeractive molecules and peptidomimetic agents. Although the preferred immunointeractive molecule is an immunoglobulin molecule, the present invention extends to other immunointeractive molecules such as antibody fragments, single chain antibodies, deimmunized antibodies including humanized antibodies and T-cell associated antigen-binding molecules (TABMs). Most preferably, the immunointeractive molecule is an antibody such as a polyclonal or monoclonal antibody. It should be understood that the subject immunointeractive molecule may be linked, bound or otherwise associated to any other proteinaceous or non-proteinaceous molecule or cell. Most preferably, the antibody is a monoclonal antibody.

The interactive molecule is "directed to" the nuclear molecule, for example La, or, to the extent that the interactive molecule is an immunointeractive molecule, to an antigenic determinant or epitope. It should be understood that the molecule may not necessarily exhibit complete exclusivity, although this is preferable. For example, antibodies are known to sometimes cross-react with other antigens. An antigenic determinant or epitope includes that part of the molecule to which an immune response can be directed. The antigenic determinant or epitope may be a B-cell epitope or where appropriate a T-cell receptor binding molecule. The term "antigenic part" includes an antigenic determinant or epitope.

Preferably, the subject immunointeractive molecule is an antibody.

Even more preferably, said antibody is a monoclonal antibody.

According to this preferred embodiment, there is provided a method for detecting an apoptotic neoplastic cell in a subject or in a biological sample from said subject, said method comprising contacting cells or cell extracts from said subject or said biological sample with an antibody directed to La or antigenic portion thereof and screening for antibody-La complex formation wherein the non-nuclear localisation of said complex is indicative of an apoptotic cell.

Preferably, said non-nuclear localisation occurs within the cytoplasm of the apoptotic cell or within the apoptotic bodies formed by the apoptotic cell.

Reference to a "biological sample" should be understood as a reference to any sample of biological material derived from an individual such as, but not limited to, mucus, stool, urine, blood, serum, cell extract, biopsy specimens and fluid which has been introduced into the body of an individual and subsequently removed such as, for example, the saline solution extracted from the lung following lung lavage or the solution retrieved from an enema wash. The biological sample which is tested according to the method of the present invention may be tested directly or may require some form of treatment prior to testing. For example, a biopsy sample may require homogenisation or sectioning prior to testing.

In accordance with the present invention, it is proposed that apoptotic cells, including apoptotic malignant or non-malignant neoplastic cells, express La extracellularly. The quantitative or qualitative detection of levels of extracellular La provides, therefore, an indicator that a cell is apoptotic and is associated with a condition characterised by cellular apoptosis.

The present invention therefore provides a method of diagnosing or monitoring a condition characterised by aberrant, unwanted or otherwise inappropriate cellular apoptosis. By "aberrant, unwanted or otherwise inappropriate" is meant that the subject apoptosis may be at an excessive level, inadequate level or at a normal level, but which level in inappropriate or otherwise unwanted. As detailed herein, there are a number of conditions which are characterised by the presence of some degree of cellular apoptosis, for example, infarction of cardiac muscle or brain tissue or autoimmune and other inflammatory diseases, or viral diseases such as AIDS, or neurogenerative diseases such as Alzheimer's disease or Parkinson's disease, or acute solid organ or bone marrow transplant rejection, or chemotherapy- or radiation-induced tissue damage ('mucositis') and neoplasms such as tumours.

Although the preferred embodiments of the present invention are directed to screening for the occurrence of apoptosis, this being indicative of the onset of a particular disease condition, there may also occur clinical situations where one is screening for a drop in the level of cellular apoptosis or the absence of apoptosis altogether. This latter situation may arise, for example, where one is monitoring the progress of a therapeutic treatment regime and a decrease in the level of apoptosis would indicate that the disease under treatment is shifting into a remissive state. It should also be understood that in some situations the absence of cellular apoptosis events may be indicative of the development of a disease condition. For example, in the course of normal thymocyte development, a large portion of the thymocytes present in the thymus undergo apoptosis during the course of the positive and negative selection events which are necessary in order to develop self/non-self discrimination. Accordingly, the absence of a normal level of cellular apoptotic events in the thymus of a young child may be indicative of the propensity of the child to developing autoimmune conditions. It should therefore be understood that although the present invention is likely to be largely applied in the context of screening for the presence of specific cellular apoptosis events in order to enable the diagnosis of a disease condition, the method of the present invention can nevertheless be applied to screening for the absence of apoptotic events, where that would indicate the development of or a propensity to develop certain disease conditions. The method of the present invention may also be applied to screening for changes in the level of cellular apoptosis in the context of monitoring the progress of a disease condition or therapeutic or prophylactic treatment regime.

Accordingly, another aspect of the present invention is directed to a method for diagnosing or monitoring a condition characterised by aberrant, unwanted or otherwise inappropriate cellular apoptosis in a subject, said method comprising contacting cells or cell extracts from said subject or a biological sample from said subject with a nuclear molecule-binding effective amount of an interactive molecule directed to said nuclear molecule or an antigenic determinant or epitope thereof and quantitatively or qualitatively detecting nuclear molecule-immunointeractive molecule complex formation wherein the non-nuclear localisation of said complex is indicative of cellular apoptosis.

Preferably, said nuclear molecule is La.

Preferably, said interactive molecule is an immunointeractive molecule and even more preferably an anti-La antibody, such as an anti-La monoclonal antibody.

Most preferably, said non-nuclear localisation is extracellular localisation and still more preferably within the cytoplasm of the apoptotic cell or within the apoptotic bodies formed by the apoptotic cell.

In another preferred embodiment, said condition is infarction of cardiac muscle or brain tissue, autoimmune and other inflammatory diseases, viral diseases such as AIDS, neurogenerative diseases such as Alzheimer's disease or Parkinson's disease, acute solid organ or bone marrow transplant rejection, chemotherapy- or radiation-induced tissue damage ('mucositis') or neoplasms such as tumours.

In a most preferred embodiment the present invention is directed to a method for diagnosing or monitoring a neoplastic condition in a subject, said method comprising contacting said cells or cell extracts from said subject or a biological sample from said subject with an La-binding effective amount of an immunointeractive molecule directed to said La or an antigenic determinant or epitope thereof and quantitatively or qualitatively detecting La-immunointeractive molecule complex formation wherein the non-nuclear localisation of said complex is indicative of cellular apoptosis and said cellular apoptosis is indicative of said neoplastic condition.

Preferably said neoplasm is central nervous system tumours, retinoblastoma, neuroblastoma and other paediatric tumours, head and neck cancers (e.g. squamous cell cancers), breast and prostate cancers, lung cancer (both small and non-small cell lung cancer), kidney cancers (e.g. renal cell adenocarcinoma), oesophagogastric cancers, hepatocellular carcinoma, pancreaticobiliary neoplasias (e.g. adenocarcinomas and islet cell tumours), colorectal cancer, cervical and anal cancers, uterine and other reproductive tract cancers, urinary tract cancers (e.g. of ureter and bladder), germ cell tumours (e.g. testicular germ cell tumours or ovarian germ cell tumours), ovarian cancer (e.g. ovarian epithelial cancers), carcinomas of unknown primary, human immunodeficiency associated malignancies (e.g. Kaposi's sarcoma), lymphomas, leukemias, malignant melanomas, sarcomas, endocrine tumours (e.g. of thyroid gland), mesothelioma and other pleural tumours, neuroendocrine tumours and carcinoid tumours.

Most preferably, said immunointeractive molecule is an antibody, and still more preferably a monoclonal antibody.

Reference herein to a "subject" should be understood to encompass humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). Preferably, the mammal is a human.

The use of antibodies and in particular monoclonal antibodies, such as those hereinbefore mentioned, to detect nuclear molecules such as La is a preferred method of the present invention. Antibodies may be prepared by any of a number of means. For the detection of human La, for example, human-human monoclonal antibody hybridomas may be derived from B cells, which have been-obtained from patients who make anti-La autoantibodies because they have systemic autoimmune diseases such as systemic lupus erythematosis (SLE) or Sjogren's syndrome (Ravirajan et al. *Lupus* 1(3):157-165, 1992). Antibodies are generally but not necessarily derived from non-human animals such as primates, livestock animals (e.g. sheep, cows, pigs, goats, horses), laboratory test animals (e.g. mice, rats, guinea pigs, rabbits) and companion animals (e.g. dogs, cats). Generally, antibody based assays are conducted in vitro on cell or tissue biopsies. However, if an antibody is suitably deimmunized or, in the case of human use, humanized, then the antibody can be labelled with, for example, a nuclear tag, administered to a patient and the site of nuclear label accumulation determined by radiological techniques. The La antibody is regarded, therefore, as a cellular apoptosis targeting agent. Accordingly, the present invention extends to deimmunized forms of the antibodies for use in cellular apoptosis imaging in human and non-human patients. This is described further below.

The present invention provides, therefore, an antibody and in particular a monoclonal antibody for use in immunological assays for La or for cellular apoptosis imaging in vivo. Currently available antibodies include SW3 and 3B9.

For the generation of antibodies to La, this molecule is required to be extracted from a biological sample whether this be from animal including human tissue or from cell culture if produced by recombinant means. The La can be separated from the biological sample by any suitable means. For example, the separation may take advantage of any one or more of La's surface charge properties, size, density, biological activity and its affinity for another entity (e.g. another protein or chemical compound to which it binds or otherwise associates). Thus, for example, separation of La from the biological fluid may be achieved by any one or more of ultra-centrifugation, ion-exchange chromatography (e.g. anion exchange chromatography, cation exchange chromatography), electrophoresis (e.g. polyacrylamide gel electrophoresis, isoelectric focussing), size separation (e.g., gel filtration, ultra-filtration) and affinity-mediated separation (e.g. immunoaffinity separation including, but not limited to, magnetic bead separation such as Dynabead™ separation, immunochromatography, immuno-precipitation). Choice of the separation technique(s) employed may depend on the biological activity or physical properties of the La sought or from which tissues it is obtained.

Preferably, the separation of La from the biological fluid preserves conformational epitopes present on the protein and, thus, suitably avoids techniques that cause denaturation of the enzyme. Persons of skill in the art will recognize the importance of maintaining or mimicking as close as possible physiological conditions peculiar to La (e.g. the biological fluid from which it is obtained) to ensure that the antigenic determinants or active sites on La, which are exposed to the animal, are structurally identical to that of the native protein. This ensures the raising of appropriate antibodies in the immunised animal that would recognize the native protein. In a preferred embodiment, La is separated from the biological fluid using any one or more of affinity separation, gel filtration and ultra-filtration.

Immunization and subsequent production of monoclonal antibodies can be carried out using standard protocols as for example described by Kohler and Milstein, *Nature* 256: 495-499, 1975; Kohler and Milstein, *Eur. J. Immunol.* 6(7): 511-519, 1976; Coligan et al., *Current Protocols in Immunology*, John Wiley & Sons, Inc., 1991-1997, or Toyama et al., "*Monoclonal Antibody, Experiment Manual*", published by Kodansha Scientific, 1987. Essentially, an animal is immunized with a La-containing biological fluid or fraction thereof by standard methods to produce antibody-producing cells, particularly antibody-producing somatic cells (e.g. B lymphocytes). These cells can then be removed from the immunized animal for immortalization.

Where a fragment of La is used to generate antibodies, it may need to first be associated with a carrier. By "carrier" is meant any substance of typically high molecular weight to which a non- or poorly immunogenic substance (e.g. a hapten) is naturally or artificially linked to enhance its immunogenicity.

Immortalization of antibody-producing cells may be carried out using methods which are well-known in the art. For example, the immortalization may be achieved by the transformation method using Epstein-Barr virus (EBV) (Kozbor et al., *Methods in Enzymology* 121: 140, 1986). In a preferred embodiment, antibody-producing cells are immortalized using the cell fusion method (described in Coligan et al., 1991-1997, supra), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of humans with circulating La-reactive antibodies, and primed animals, preferably rodent animals such as mice and rats. Mice spleen cells are particularly useful. It would be possible, however, to use rat, rabbit, sheep or goat cells, or cells from other animal species instead.

Specialized myeloma cell lines have been developed from lymphocytic tumours for use in hybridoma-producing fusion procedures (Kohler and Milstein, 1976, supra; Shulman et al., *Nature* 276: 269-270, 1978; Volk et al., *J. Virol.* 42(1): 220-227, 1982). These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumour cells to produce their own antibodies. To eliminate the production of tumour cell antibodies by the hybridomas, myeloma cell lines incapable of producing endogenous light or heavy immunoglobulin chains are used. A third reason for selection of these cell lines is for their suitability and efficiency for fusion.

Many myeloma cell lines may be used for the production of fused cell hybrids, including, e.g. P3X63-Ag8, P3X63-AG8.653, P3/NS1-Ag4-1 (NS-1), Sp2/0-Ag14 and S194/5.XXO.Bu.1. The P3X63-Ag8 and NS-1 cell lines have been described by Köhler and Milstein (1976, supra). Shulman et al. (1978, supra) developed the Sp2/0-Ag14 myeloma line. The S194/5.XXO.Bu.1 line was reported by Trowbridge, *J. Exp. Med.* 148(1): 313-323, 1978.

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Kohler and Milstein, 1975, supra; 1976, supra; Gefter et al., *Somatic Cell Genet.* 3: 231-236, 1977; Volk et al., 1982, supra). The fusion-promoting agents used by those investigators were Sendai virus and polyethylene glycol (PEG).

Because fusion procedures produce viable hybrids at very low frequency (e.g. when spleens are used as a source of somatic cells, only one hybrid is obtained for roughly every $1 \times 10^5$ spleen cells), it is preferable to have a means of selecting the fused cell hybrids from the remaining unfused cells, particularly the unfused myeloma cells. A means of detecting the desired antibody-producing hybridomas among other resulting fused cell hybrids is also necessary. Generally, the selection of fused cell hybrids is accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radio-immunoassay techniques as, for example, described in Kennet et al. (eds) *Monoclonal Antibodies and Hybridomas: A New Dimension in Biological Analyses*, pp. 376-384, Plenum Press, New York, 1980 and by FACS analysis.

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumours that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines are tested for their specificity to detect the La by any suitable immunodetection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target La but which does not recognize non-target epitopes are identified and then directly cultured in vitro or injected into a histocompatible animal to form tumours and to produce, collect and purify the required antibodies.

These antibodies are La specific. This means that the antibodies are capable of distinguishing La from other molecules. More broad spectrum antibodies may be used provided that they do not cross react with molecules in a normal cell.

In a preferred embodiment, the subject antibody is anti-human La monoclonal antibodies, 8G3 and 9A5 (Bachmann et al. *Proc Natl Acad Sci USA* 83 (20):7770-7774, 1986), anti-human La monoclonal antibody (mAb), La1B5 (Mamula et al. *J Immunol* 143(9):2923-2928, 1989), anti-human La monoclonal antibodies (Carmo-Fonseca et al. *Exp Cell Res* 185(1):73-85, 1989), anti-human and anti-bovine La monoclonal antibodies, SW1, SW3 and SW5 (Pruijn et al. *Eur J Biochem* 232(2):611-619, 1995), anti-human and anti-rodent La mAb, La4B6 (Troster et al. *J Autoimmunity* 8(6): 825-842, 1995) or anti-human and anti-murine La mAb, 3B9 (Tran et al. *Arthritis Rheum* 46(1):202-208, 2002) or derivative, homologue, analogue, chemical equivalent, mutant or mimetic thereof.

The present invention should also be understood to extend to the immunointeractive molecule and the cell lines which express the subject immunointeractive molecule, in particular a hybridoma which expresses a monoclonal antibody.

Where the monoclonal antibody is destined for use in in vivo imaging or treatment, it may need to be deimmunized with respect to the host into which it will be introduced (e.g. a human). The deimmunization process may take any of a number of forms including the preparation of chimeric antibodies which have the same or similar specificity as the monoclonal antibodies prepared according to the present invention. Chimeric antibodies are antibodies whose light and heavy chain genes have been constructed, typically by genetic engineering, from immunoglobulin variable and constant region genes belonging to different species. Thus, in accordance with the present invention, once a hybridoma producing the desired monoclonal antibody is obtained, techniques are used to produce interspecific monoclonal antibodies wherein the binding region of one species is combined with a non-binding region of the antibody of another species (Liu et al., *Proc. Natl. Acad. Sci. USA* 84: 3439-3443, 1987). For example, complementary determining regions (CDRs) from a non-human (e.g. murine) monoclonal antibody can be grafted onto a human antibody, thereby "humanizing" the murine antibody (European Patent Publication No. 0 239 400; Jones et al., *Nature* 321: 522-525, 1986; Verhoeyen et al., *Science* 239: 1534-1536, 1988; Richmann et al., *Nature* 332: 323-327, 1988). In this case, the deimmunizing process is specific for humans. More particularly, the CDRs can be grafted onto a human antibody variable region with or without human constant regions. The non-human antibody providing the CDRs is typically referred to as the "donor" and the human antibody providing the framework is typically referred to as the "acceptor". Constant regions need not be present, but if they are, they must be substantially identical to human immunoglobulin constant regions, i.e. at least about 85-90%, preferably about 95% or more identical. Hence, all parts of a humanized antibody, except possibly the CDRs, are substantially identical to corresponding parts of natural human immunoglobulin sequences. Thus, a "humanized antibody" is an antibody comprising a humanized light chain and a humanized heavy chain immunoglobulin. A donor antibody is said to be "humanized", by the process of "humanization", because the resultant humanized antibody is expected to bind to the same antigen as the donor antibody that provides the CDRs. Reference herein to "humanized" includes reference to an antibody deimmunized to a particular host, in this case, a human host.

It will be understood that the deimmunized antibodies may have additional conservative amino acid substitutions which have substantially no effect on antigen binding or other immunoglobulin functions. Exemplary conservative substitutions may be made according to Table 1.

TABLE 1

| ORIGINAL RESIDUE | EXEMPLARY SUBSTITUTIONS |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Exemplary methods which may be employed to produce deimmunized antibodies according to the present invention are described, for example, in references Richmann et al., 1988, supra; European Patent Publication No. 0 239 400; Chou et al. (U.S. Pat. No. 6,056,957); Queen et al. (U.S. Pat. No. 6,180,370); Morgan et al. (U.S. Pat. No. 6,180,377).

Thus, in one embodiment, the present invention contemplates a deimmunized antibody molecule having specificity for an epitope recognized by a monoclonal antibody to La wherein at least one of the CDRs of the variable domain of said deimmunized antibody is derived from the said monoclonal antibody to La and the remaining immunoglobulin-derived parts of the deimmunized antibody molecule are derived from an immunoglobulin or an analogue thereof from the host for which the antibody is to be deimmunized.

This aspect of the present invention involves manipulation of the framework region of a non-human antibody.

The present invention extends to mutants, analogues and derivatives of the subject antibodies but which still retain specificity for La.

The terms "mutant" or "derivatives" includes one or more amino acid substitutions, additions and/or deletions.

As used herein, the term "CDR" includes CDR structural loops which covers the three light chain and the three heavy chain regions in the variable portion of an antibody framework region which bridge β strands on the binding portion of the molecule. These loops have characteristic canonical structures (Chothia et al., *J. Mol. Biol.* 196: 901, 1987; Chothia et al., *J. Mol. Biol.* 227: 799, 1992).

By "framework region" is meant region of an immunoglobulin light or heavy chain variable region, which is interrupted by three hypervariable regions, also called CDRs. The extent of the framework region and CDRs have been precisely defined (see, for example, Kabat et al., "*Sequences of Proteins of Immunological Interest*", U.S. Department of Health and Human Services, 1983). The sequences of the framework regions of different light or heavy chains are relatively conserved within a species. As used herein, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of La.

As used herein, the term "heavy chain variable region" means a polypeptide which is from about 110 to 125 amino acid residues in length, the amino acid sequence of which corresponds to that of a heavy chain of a monoclonal antibody of the invention, starting from the amino-terminal (N-terminal) amino acid residue of the heavy chain. Likewise, the term "light chain variable region" means a polypeptide which is from about 95 to 130 amino acid residues in length, the amino acid sequence of which corresponds to that of a light chain of a monoclonal antibody of the invention, starting from the N-terminal amino acid residue of the light chain. Full-length immunoglobulin "light chains" (about 25 Kd or 214 amino acids) are encoded by a variable region gene at the $NH_2$-terminus (about 110 amino acids) and a κ or λ constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g. γ (encoding about 330 amino acids).

The term "immunoglobulin" or "antibody" is used herein to refer to a protein consisting of one or more polypeptides substantially encoded by immunoglobulin genes. The recognized immunoglobulin genes include the κ, λ, α, γ ($IgG_1$, $IgG_2$, $IgG_3$, $IgG_4$), δ, ε and μ constant region genes, as well as the myriad immunoglobulin variable region genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and $(Fab')_2$.

The invention also contemplates the use and generation of fragments of monoclonal antibodies produced by the method of the present invention including, for example, Fv, Fab, Fab' and $F(ab')_2$ fragments. Such fragments may be prepared by standard methods as for example described by Coligan et al. (1991-1997, supra).

The present invention also contemplates synthetic or recombinant antigen-binding molecules with the same or similar specificity as the monoclonal antibodies of the invention. Antigen-binding molecules of this type may comprise a synthetic stabilised Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Krebber et al. (Krebber et al., *J. Immunol. Methods* 201(1): 35-55, 1997). Alternatively, they may be prepared by methods described in U.S. Pat. No. 5,091,513, European Patent No 239,400 or the articles by Winter and Milstein (Winter and Milstein, *Nature* 349: 293, 1991) and Plückthun et al. (Plückthun et al., In *Antibody engineering: A practical approach* 203-252, 1996).

Alternatively, the synthetic stabilized Fv fragment comprises a disulphide stabilized Fv (dsFv) in which cysteine residues are introduced into the $V_H$ and $V_L$ domains such that in the fully folded Fv molecule the two residues will form a disulphide bond therebetween. Suitable methods of producing dsFv are described, for example, in (Glockshuber et al., *Biochem.* 29: 1363-1367, 1990; Reiter et al., *Biochem.* 33: 5451-5459, 1994; Reiter et al., *Cancer Res.* 54: 2714-2718, 1994; Reiter et al., *J. Biol. Chem.* 269: 18327-18331, 1994; Webber et al., *Mol. Immunol.* 32: 249-258, 1995).

Also contemplated as synthetic or recombinant antigen-binding molecules are single variable region domains (termed dabs) as, for example, disclosed in (Ward et al., *Nature* 341: 544-546, 1989; Hamers-Casterman et al., *Nature* 363: 446-448, 1993; Davies & Riechmann, *FEBS Lett.* 339: 285-290, 1994).

Alternatively, the synthetic or recombinant antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the synthetic or recombinant antigen binding molecule may comprise non-immunoglobulin derived, protein frameworks. For example, reference may be made to (Ku & Schutz, *Proc. Natl. Acad. Sci. USA* 92: 6552-6556, 1995) which discloses a four-helix bundle protein cytochrome b562 having two loops randomized to create CDRs, which have been selected for antigen binding.

The synthetic or recombinant antigen-binding molecule may be multivalent (i.e. having more than one antigen binding site). Such multivalent molecules may be specific for one or more antigens. Multivalent molecules of this type may be prepared by dimerization of two antibody fragments through a cysteinyl-containing peptide as, for example disclosed by (Adams et al., *Cancer Res.* 53: 4026-4034, 1993; Cumber et al., *J. Immunol.* 149: 120-126, 1992). Alternatively, dimerization may be facilitated by fusion of the antibody fragments to amphiphilic helices that naturally dimerize (Plünckthun, *Biochem.* 31: 1579-1584, 1992) or by use of domains (such as leucine zippers jun and fos) that preferentially heterodimerize (Kostelny et al., *J. Immunol.* 148: 1547-1553, 1992).

The present invention further encompasses chemical analogues of amino acids in the subject antibodies. The use of chemical analogues of amino acids is useful inter alia to stabilize the molecules such as if required to be administered to a subject. The analogues of the amino acids contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with NaBH; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide. Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |

TABLE 2-continued

| Non-conventional amino acid | Code | Non-conventional amino acid | Code |
|---|---|---|---|
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups with n = 1 to n = 6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH).

The present invention further contemplates an assay to detect an apoptotic cell in a biological sample, said assay including the steps of:

(3) contacting an interactive molecule directed to a nuclear molecule or an antigenic determinant thereof with a biological sample suspected of containing said nuclear molecule; and (4) subjecting the complex formed in step (1) to a signal detection step wherein detecting non-nuclear interactive molecule-nuclear molecule complex formation is indicative of apoptotic cells.

Preferably, said nuclear molecule is La.

More preferably, said interactive molecule is an immunointeractive molecule and even more preferably an anti-La antibody, such as the monoclonal antibodies SW3 or 3B9.

Most preferably, said non-nuclear localisation is extracellular localisation and, still more preferably, localisation within the cytoplasm of the apoptotic cell or within the apoptotic bodies formed by the apoptotic cells.

The signal detection step may include ELISA or any other reporter molecule based assays. As part of this detection step, the signal may first need to be amplified. It should be understood that this assay may be performed in vivo or in vitro.

A deimmunized monoclonal antibody of the present invention may also be useful for apoptosis imaging in vivo as well as for targeting apoptotic cells in order to bring the apoptotic cells into contact with bystander-cell growth retarding or bystander-cell killing agents, i.e. cytostatic or cytocidal agents.

Anti-La antibodies are superior to currently known products, such as Apomate™ (North American Scientific, Inc.), for the detection of apoptotic cells in vivo. Apomate™ uses radiolabeled annein V to bind apoptotic cells and, in particular, to ascertain the responsiveness of cancers to chemotherapy. Annexin V binds to phosphatidylserine that 'flip-flops' to the outer plasma membrane leaflet during the early part of apoptosis. However, the detection of chemotherapy-induced tumour cell apoptosis by Apomate™ is inconsistent because the timing of administration may be crucial (Blankenberg et al. *Clin Cancer Res* 2002). Timing is less important with the use of anti-La antibodies because the antibodies direct apoptotic cells to macrophages, which accumulate at the site of cancers. Moreover, annexin V inhibits macrophage-mediated phagocytosis of apoptotic thymocytes in vitro, which is circumvented by Fc receptor-mediated uptake of antibody-bound erythrocytes, which have surface-exposed phosphatidylserine (Callahan et al. *Cell Death Different* 7(7): 645-653, 2000; Krahlung et al. *Cell Death Different* 6(2):183-189, 1999). Hence, anti-La antibodies opsonise apoptotic cells and facilitate their phagocytosis by macrophages, in particular, so that macrophages are targeted for diagnostic and/or therapeutic purposes, as hereinafter described in more detail. Accordingly, one of the advantages of the use of anti-La antibodies, as opposed to currently known diagnostic methods such as those based on detecting Annexin V, is that the opsonisation and uptake of apoptotic cells by macrophages results in accumulation of the antibody in macrophages at the site of the apoptotic cells, thereby aiding imaging.

With respect to imaging, a reporter molecule is attached to the deimmunized monoclonal antibody and this is then introduced to a host, such as a human. By detecting the reporter molecule, cellular apoptotic clusters, such as those associated with tumours, can be visualized. One particularly useful form of reporter molecule is a nuclear tag. Some radioisotopes permit imaging by positron emission tomography (PET) and some ligands facilitate detection of target binding by magnetic resonance imaging (MRI).

Accordingly, another aspect of the present invention contemplates a method for detecting apoptotic cells in a human, said method comprising introducing into said patient an interactive molecule directed to a nuclear molecule or an antigenic determinant thereof labelled with a reporter molecule, allowing dissemination of the labelled interactive molecule throughout the circulatory system, or to selected parts of the circulatory system and then subjecting said patient to reporter molecule-detection means to identify the location of the interactive molecule.

Preferably, said nuclear molecule is La.

More preferably, said interactive molecule is an immunointeractive molecule and even more preferably an anti-La antibody.

Most preferably, said non-nuclear localisation is extracellular localisation and preferably, localisation within the cytoplasm of the apoptotic cell or within the apoptotic bodies formed by the apoptotic cells.

Preferably said apoptotic cells are characteristic of a neoplasm.

Preferably said neoplastic cell is one which is characteristic of central nervous system tumours, retinoblastoma, neuroblastoma and other paediatric tumours, head and neck cancers (e.g. squamous cell cancers), breast and prostate cancers, lung cancer (both small and non-small cell lung cancer), kidney cancers (e.g. renal cell adenocarcinoma), oesophago-gastric cancers, hepatocellular carcinoma, pancreaticobiliary neoplasias (e.g. adenocarcinomas and islet cell tumours), colorectal cancer, cervical and anal cancers, uterine and other reproductive tract cancers, urinary tract cancers (e.g. of ureter and bladder), germ cell tumours (e.g. testicular germ cell tumours or ovarian germ cell tumours), ovarian cancer (e.g. ovarian epithelial cancers), carcinomas of unknown primary, human immunodeficiency associated malignancies (e.g. Kaposi's sarcoma), lymphomas, leukemias, malignant melanomas, sarcomas, endocrine tumours (e.g. of thyroid gland), mesothelioma and other pleural tumours, neuroendocrine tumours and carcinoid tumours.

Immunologically based La detection protocols may take a variety of forms. For example, a plurality of antibodies may be immobilized in an array each with different specificities to particular antigens or cancer cells including La. Cells from a biopsy are then brought into contact with the antibody array and a diagnosis may be made as to the type of neoplasm based on the cells which are immobilized.

Other more conventional assays may also be conducted such as by ELISA, Western blot analysis, immunoprecipitation analysis, immunofluorescence analysis, immunochemistry analysis or FACS analysis.

The present invention provides, therefore, a method of detecting, in a sample, La or fragment, variant or derivative thereof comprising contacting the sample with an antibody or fragment or derivative thereof and detecting the formation of a complex comprising said antibody and La or fragment, variant or derivative thereof wherein non-nuclear localisation of La is indicative of apoptosis.

Preferably, said non-nuclear localisation is extracellular localisation and, still more preferably, localisation within the cytoplasm of the apoptotic cell or within the apoptotic bodies formed by the apoptotic cell.

As discussed above, any suitable technique for determining formation of the complex may be used. For example, an antibody according to the invention, having a reporter molecule associated therewith, may be utilized in immunoassays. Such immunoassays include but are not limited to radioimmunoassays (RIAs), enzyme-linked immunosorbent assays (ELISAs) and immunochromatographic techniques (ICTs), Western blotting which are well known to those of skill in the art. For example, reference may be made to "Current Protocols in Immunology", 1994 which discloses a variety of immunoassays which may be used in accordance with the present invention. Immunoassays may include competitive assays. It will be understood that the present invention encompasses qualitative and quantitative immunoassays.

Suitable immunoassay techniques are described, for example, in U.S. Pat. Nos. 4,016,043, 4,424,279 and 4,018,653. These include both single-site and two-site assays of the non-competitive types, as well as the traditional competitive binding assays. These assays also include direct binding of a labelled antigen-binding molecule to a target antigen. The antigen in this case is La or a fragment thereof.

Two-site assays are particularly favoured for use in the present invention. A number of variations of these assays exist, all of which are intended to be encompassed by the present invention. Briefly, in a typical forward assay, an unlabelled antigen-binding molecule such as an unlabelled antibody is immobilized on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including minor variations as will be readily apparent.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labelled antibody that binds, as determined by the associated reporter molecule, is proportional to the amount of antigen bound to the immobilized first antibody.

An alternative method involves immobilizing the antigen in the biological sample and then exposing the immobilized antigen to specific antibody that may or may not be labelled with a reporter molecule. Depending on the amount of target and the strength of the reporter molecule signal, a bound antigen may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

From the foregoing, it will be appreciated that the reporter molecule associated with the antigen-binding molecule may include the following:
(a) direct attachment of the reporter molecule to the antibody;
(b) indirect attachment of the reporter molecule to the antibody; i.e., attachment of the reporter molecule to another assay reagent which subsequently binds to the antibody; and
(c) attachment to a subsequent reaction product of the antibody.

The reporter molecule may be selected from a group including a chromogen, a catalyst, an enzyme, a fluorochrome, a chemiluminescent molecule, a paramagnetic ion, a lanthanide ion such as Europium ($Eu^{34}$), a radioisotope including other nuclear tags, semiconductor quantum dots (Wu et al. *Nature Biotechnol* 2002) and a direct visual label. Recombinant antibody-like molecules may be made by fusion to partners such as enhanced green fluorescent protein (EGFP).

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al., International Publication No. WO 93/06121. Reference also may be made to the fluorochromes described in U.S. Pat. No. 5,573,909, Singer et al., and U.S. Pat. No. 5,326,692 Brinkley et al. Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

In the case of an enzyme immunoassay, an enzyme is conjugated to the second antibody, generally by means of glutaraldehyde or periodate. As will be readily recognized, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex, allowed to bind, and then the excess reagent washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthanide, europium (EU), may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules may also be employed.

The method of the present invention is useful as a one off test or as an on-going monitor of those individuals thought to be at risk of development or a condition characterised by cellular apoptosis (e.g. neoplasm) or as a monitor of the effectiveness of therapeutic or prophylactic treatment regimes directed to inhibiting or otherwise slowing the progress of such a condition. In these situation, mapping the modulation of La levels in any one or more classes of biological samples is a valuable indicator of the status of an individual or the effectiveness of a therapeutic or prophylactic regime which is currently in use. Accordingly, the method of the present invention should be understood to extend to monitoring for increases or decreases in marker levels in an individual relative to their normal level (as hereinbefore defined) or relative to one or more earlier marker levels determined from a biological sample of said individual.

The present invention further contemplates the use of an interactive molecule directed to a nuclear molecule in the manufacture of a quantitative or semi-quantitative diagnostic kit to detect apoptotic cells in a biological sample from a patient. The kit may come with instructions for use and may be automated or semi-automated or in a form which is compatible with automated machine or software.

Preferably, said nuclear molecule is La.

Preferably, said apoptotic cells are apoptotic neoplastic cells.

Without limiting the applications for the kit in any way, it is useful for the detection of apoptotic cells in diagnostic and research applications. Currently, there are many reagents on the market for the detection of apoptosis in vitro, which include annexin V, mitochondrial permeability dyes, APO2.7 (a monoclonal antibody that recognises a mitochondrial protein only during apoptosis), DNA binding fluorochromes such as propidium iodide and 7-amino-actinomycin D (7-AAD), and fluorogenic caspase inhibitors. However, these reagents are unable to distinguish between apoptotic and necrotic cells (H. Lecoeur et al. *J Immunol Methods* 2002) and more than one is required to specifically identify late apoptotic cells (P. Smolewski et al. *J. Immunol Methods* 2002; Hamel et al. *Cytometry* 25(2):173-181, 1996).

The generation of antibodies to La may, in accordance with the present invention, be directed to the active or inactive forms of the molecule.

In addition to the clear diagnostic benefits of the method of the present invention, the ability to accurately target apoptotic cells now provides a means of delivering therapeutic and/or prophylactic treatments in a localised and highly targeted manner. To date, such treatments (often referred to as "magic bullets") have not been possible. In particular, in the context of tumour therapy the notion of targeted treatments has not been possible due to the fact that it has not been possible to identify suitable tumour specific antigens against which an antibody could be directed. However, the present invention overcomes these shortcomings by directing the therapeutic or prophylactic treatment to the apoptotic cells which comprise the subject tumour. By selecting therapeutic or prophylactic effector mechanisms which can be coupled to an anti-La immunointeractive molecule, but which function on cells located proximally to the apoptotic cells, that is the non-apoptotic tumour cells, effective killing of the tumour can be achieved. The subject effector mechanism may take any suitable form but will preferably deliver a toxic molecule or otherwise kill the proximally located non-apoptotic tumour cells.

Further, the phagocytosis of apoptotic cells, which have been opsonised with anti-La antibodies, will be facilitated by antibodies such as human IgGI and IgG3. Without limiting the present invention to any one theory or mode of action, anti-La antibodies will become targeted to and accumulate in macrophages or other phagocytic cells in vivo. Cells that undergo apoptosis are first divided into membrane-bound parcels or apoptotic bodies, which are subsequently disposed of by surrounding cells and, in particular, by professional scavenger cells known as macrophages. Anti-La antibodies recognize apoptotic cells specifically at a particular stage in the apoptotic process both in vitro and in vivo. Moreover, anti-La antibodies preferentially localize in vivo to macrophages, which engulf the apoptotic cells. Macrophages contribute to the healing of the tissue damage that occurs in heart attach, stroke and organ transplant rejection. Cancers have a high content of macrophages known as tumour associated macrophages, which may either retard or promote the growth of the cancer. Hence, anti-La antibodies serve as a vehicle for the delivery of therapeutically active technologies to cancers.

Accordingly, another aspect of the present invention is directed to a method of therapeutically and/or prophylactically treating a condition in a subject, which condition is characterised by cellular apoptosis, said method comprising administering to said subject an effective amount of an interactive molecule directed to a nuclear molecule or antigenic portion thereof, which interactive molecule is linked, bound or otherwise associated with a therapeutic or prophylactic effector mechanism, for a time and under conditions sufficient to treat said condition.

Preferably, said nuclear molecule is La.

More preferably, said interactive molecule is an immunointeractive molecule and even more preferably an anti-La antibody.

In another preferred embodiment, said condition is infarction of cardiac muscle or brain tissue, autoimmune and other inflammatory diseases, viral diseases such as AIDS, neurogenerative diseases such as Alzheimer's disease or Parkinson's disease, acute solid organ or bone marrow transplant rejection, chemotherapy- or radiation-induced tissue damage ('mucositis') or neoplasms such as tumours.

Examples of neoplasms and neoplastic cells encompassed by the present invention include, but are not limited central nervous system tumours, retinoblastoma, neuroblastoma and other paediatric tumours, head and neck cancers (e.g. squamous cell cancers), breast and prostate cancers, lung cancer (both small and non-small cell lung cancer), kidney cancers (e.g. renal cell adenocarcinoma), oesophagogastric cancers, hepatocellular carcinoma, pancreaticobiliary neoplasias (e.g. adenocarcinomas and islet cell tumours), colorectal cancer, cervical and anal cancers, uterine and other reproductive tract cancers, urinary tract cancers (e.g. of ureter and bladder), germ cell tumours (e.g. testicular germ cell tumours or ovarian germ cell tumours), ovarian cancer (e.g. ovarian epithelial cancers), carcinomas of unknown primary, human immunodeficiency associated malignancies (e.g. Kaposi's sarcoma), lymphomas, leukemias, malignant melanomas, sarcomas, endocrine tumours (e.g. of thyroid gland), mesothelioma and other pleural tumours, neuroendocrine tumours and carcinoid tumours.

Reference to "nuclear molecule", "La", "immunointeractive molecule", "subject" and "apoptosis" should be understood to have the same meaning as hereinbefore provided.

The present invention more particularly provides a method of therapeutically and/or prophylactically treating a neoplastic condition in a subject, said method comprising administering to said subject an effective amount of an immunointeractive molecule directed to La or antigenic portion thereof, which immunointeractive molecule is linked, bound or otherwise associated with a therapeutic effector mechanism, for a time and under conditions sufficient to inhibit, reduce or otherwise down-regulate the growth of the neoplasm.

Preferably said neoplastic condition is a malignant tumour.

Reference to an "effector mechanism" should be understood as a reference to any suitable mechanism which, when localised to the site of apoptotic cells, either directly or indirectly treats the condition in issue, for example, down-regulating the growth of tumour cells. In the context of this preferred embodiment, the effector mechanism is most likely a proteinaceous or non-proteinaceous molecule or group of molecules which achieve this outcome. Examples of effector mechanisms suitable for use in the method of the present invention include, but are not limited to:

(i) Use of an antibody which has been linked to a cytokine, chemokine or other factor, such as macrophage, dendritic cell and/or T cell activators which act to induce or enhance one or more aspects of an immune response, thereby augmenting bystander killing. For example, the chemotactic peptide, N-formyl-methionyl-leucyl-phenylalanine (FMLP) (Morikawa et al. *Cancer Immunol Immunother* 27(1):1-6, 1988) and the novel bacterial lipopeptide, JBT 2002 (Shinohara et al. *J Immunother* 23(3):321-331, 2000) are both activators of tumour associated macrophages.

(ii) Use of an antibody which has been conjugated to a toxin.
Reference to "toxin" should be understood as a reference to any suitable proteinaceous or non-proteinaceous molecule which achieves the object of providing a signal which reduces, prevents or otherwise inhibits the proliferation, differentiation or maintenance of the subject cell (herein referred to as "down-regulating the growth" of said cell). The subject toxin may act by a variety of means including providing its signal via direct contact with a subject cell or emitting a molecule or particle, such as radiation in the case of a radioactive isotope toxin, which provides the signal to the subject cell. Preferably the toxin is a radioisotope and even more preferably a radioisotope which is highly toxic over a short range and exhibits a short half life thereby minimizing the occurrence of inadvertent toxicity on proximally located non-target cells. Most particularly, said radioisotope is an alpha particle emitting radioisotope. However, it should be understood that radioisotopes are not limited to alpha particle emitting radioisotope and may include beta- and gamma-emitting radioisotopes, depending on the clinical context. Examples of alpha-emitting radioisotopes suitable for use in the method of the present invention include, but are not limited to, Tb-149 or Bi-213. It should be understood that the toxin which is utilised in the method of the present invention may be in a purified, partially purified or unpurified form. It may also form a component of a larger molecule. The toxin may be naturally occurring or it may be synthetically or recombinantly produced.

Other examples of molecules which should be understood to fall within the scope of "toxin" include ricin, colicheamicin, prodrugs (as antibody-directed prodrug converting enzyme therapy [ADEPT]) and novel biotherapeutic agents, such as catalytic antibodies.

It should be understood that the method of the present invention may be performed either in vivo or in vitro. Examples of in vitro applications include, but are not limited to, the in vitro purging of biological samples comprising neoplastic cells. For example, bone marrow and/or blood may be removed from a patient, purged to kill tumour cells in accordance with the method of the present invention and then returned to the patient. Such procedures are currently performed, albeit in a significantly less targeted manner, and avoid the significant risks associated with the transplantation of MHC incompatible bone marrow.

Reference to an effector mechanism being "linked, bound or otherwise associated" with an anti-La, for example, antibody or other immunointeractive molecule should be understood as a reference to any covalent or non-covalent interactive mechanism which achieves linking of the two molecules. This includes, but is not limited to the use of peptide bonds, ionic bonds, hydrogen bonds, van Der Waals forces or any other interactive bonding mechanism.

Reference to "growth" of a cell or neoplasm should be understood as a reference to the proliferation, differentiation and/or maintenance of viability of the subject cell, while "down-regulating the growth" of a cell or neoplasm is a reference to the process of cellular senescence or to reducing, preventing or inhibiting the proliferation, differentiation and/or maintenance of viability of the subject cell. In a preferred embodiment the subject growth is proliferation and the subject down-regulation is killing. In this regard, killing may be achieved either by delivering a fatal hit to the cell or by delivering to the cell a signal which induces the cell to apoptose.

Reference herein to "therapeutic" or "prophylactic" "treatment" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

Without limiting the present invention to any one theory or mode of action anti-cancer treatments usually kill by apoptosis but in many cases of advanced cancer, some cancer cells are resistant to the apoptosis that may be induced by a particular anti-cancer treatment. These apoptosis-resistant tumour cells are the source of clinical relapse of disease that ultimately kills most patients with advanced cancers and a significant proportion of those patients with earlier stage cancers. In those patients with advanced cancers who could be shown to be responding to the initial modality of treatment because tumour cell kill could be documented in vivo, additional gains in survival and quality of life may be made if another non-cross resistant treatment modality were also to be employed. Therefore, diagnosis of responding cancer patients using the method of the present invention can identify those patients who could benefit from supplementary treatment with therapeutic conjugates or hybrid fusion proteins, as detailed.

The use of an anti-La antibody may also be favoured in the adjuvant clinical setting. Although early stage breast and colon cancers can both be cured by surgery, the risk of overt and incurable systemic relapse is heightened because, in those patients whose primary tumour has certain high-risk features and/or whose regional lymph nodes contain metastases, undetectable systemic micrometastases may already exist. So the use of adjuvant chemotherapy and/or adjuvant hormonal therapy (in the case of breast cancer) cures an additional minor proportion of these patients presumably because the systemic micrometastases are cleared successfully.

Further, although dormant tumours remain small because they lack a blood supply, the tumour cells within the lesion turnover at a rapid rate with the rate of cell division balancing the rate of apoptosis. Therefore, even dormant tumours will be suitable targets for the present technology. Both in the case of clinically evident metastases and micrometastases, apoptosis-resistant cancer cells can be admixed with susceptible cancer cells. Bystander killing of these surviving cancer cells can occur if a non-cross resistant and/or synergistic means of tumour killing were delivered to nearby cancer cells that had been rendered apoptotic by the first treatment. Additional technologies that arm this technology with bystander killing potential can improve its therapeutic efficacy.

A most preferred embodiment of the present invention is therefore directed to the treatment of a metastatic cancer.

According to this preferred embodiment, there is provided a method of therapeutically treating a metastatic cancer in a subject, said method comprising administering to said subject an effective amount of an immunointeractive molecule directed to La or antigenic portion thereof, which immunointeractive molecule is linked, bound or otherwise associated with a therapeutic effector mechanism, for a time and under conditions sufficient to inhibit, reduce or otherwise downregulate the growth of said metastatic cancer.

As detailed hereinbefore, the present invention should also be understood to extend to the down-regulation of growth of neoplastic cells in an in vitro environment. For example, neoplastic cells may be purged from an inoculum of bone marrow or peripheral blood stem cells before an autologous transplant.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

The present invention further contemplates a combination of therapies, such as the administration of the antibody together with subjection of the mammal to circulating cytotoxic agents or to radiotherapy in the treatment of cancer.

Administration of the interactive molecule (herein referred to as the "modulatory agent"), in the form of a pharmaceutical composition, may be performed by any convenient means. The modulatory agent of the pharmaceutical composition is contemplated to exhibit therapeutic activity when administered in an amount which depends on the particular case. The variation depends, for example, on the human or animal and the modulatory agent chosen. A broad range of doses may be applicable. Considering a patient, for example, from about 0.1 mg to about 1 mg of modulatory agent may be administered per kilogram of body weight per day. Dosage regimes may be adjusted to provide the optimum therapeutic response. For example, several divided doses may be administered continuously, daily, weekly, monthly or other suitable time intervals or the dose may be proportionally reduced as indicated by the exigencies of the situation.

The modulatory agent may be administered in a convenient manner such as by the oral, intravenous (where water soluble), intraperitoneal, intramuscular, subcutaneous, intradermal or suppository routes or implanting (e.g. using slow release molecules). The modulatory agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

Routes of administration include, but are not limited to, respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip patch and implant.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. For example, the subject agent may be administered together with an agonistic agent in order to enhance its effects. By "sequential" administration is meant a time difference of from seconds, minutes, hours or days between the administration of the two types of molecules. These molecules may be administered in any order.

Another aspect of the present invention contemplates the use of an anti-nuclear molecule interactive molecule conjugated to an effector mechanism, in the manufacture of medicament for the treatment of a condition in a subject, which condition is characterised by cellular apoptosis, wherein said effector mechanism treats said condition.

Preferably, said nuclear molecule is La.

Preferably, said interactive molecule is an immunointeractive molecule and even more preferably an anti-La antibody, such as a monoclonal antibody.

Most preferably, said non-nuclear localisation is extracellular localisation, as hereinbefore defined.

In another preferred embodiment, said condition is infarction of cardiac muscle or brain tissue, autoimmune and other inflammatory diseases, viral diseases such as AIDS, neurogenerative diseases such as Alzheimer's disease or Parkinson's disease, acute solid organ or bone marrow transplant rejection, chemotherapy- or radiation-induced tissue damage ('mucositis') or neoplasms such as tumours.

Examples of neoplasms and neoplastic cells encompassed by the present invention include, but are not limited central nervous system tumours, retinoblastoma, neuroblastoma and other paediatric tumours, head and neck cancers (e.g. squamous cell cancers), breast and prostate cancers, lung cancer (both small and non-small cell lung cancer), kidney cancers (e.g. renal cell adenocarcinoma), oesophagogastric cancers, hepatocellular carcinoma, pancreaticobiliary neoplasias (e.g. adenocarcinomas and islet cell tumours), colorectal cancer, cervical and anal cancers, uterine and other reproductive tract cancers, urinary tract cancers (e.g. of ureter and bladder), germ cell tumours (e.g. testicular germ cell tumours or ovarian germ cell tumours), ovarian cancer (e.g. ovarian epithelial cancers), carcinomas of unknown primary, human immunodeficiency associated malignancies (e.g. Kaposi's sarcoma), lymphomas, leukemias, malignant melanomas, sarcomas, endocrine tumours (e.g. of thyroid gland), mesothelioma and other pleural tumours, neuroendocrine tumours and carcinoid tumours.

In yet another further aspect, the present invention contemplates a pharmaceutical composition comprising the modulatory agent as hereinbefore defined together with one or more pharmaceutically acceptable carriers and/or diluents. Said agents are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it win be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Yet another aspect of the present invention relates to the agent as hereinbefore defined, when used in the method of the present invention.

The present invention is further defined by the following non-limiting examples:

EXAMPLE 1

Anti-La antibody used herein is mouse monoclonal antibody hybridoma 3B9, which recognises both the human and mouse versions of the small ribonucleoprotein antigen, La/SS-B. The antibody was sourced from Professor Tom Gordon, Flinders Medical Centre, Adelaide, South Australia, who had in turn obtained it from Dr. M. Bachmann of the Oklahoma Medical Research Foundation, Oklahoma City, Okla., USA. 3B9 was published by Dr. Gordon's group (Tran et al. 2002a). The corresponding isotype control antibody hybridoma is Sal5.

Six wild type (ST) C57BL/6 male mice (seven weeks old) or two six month-old TRansgenic Adenocarcinoma of Mouse Prostate (TRAMP) mice (column 1) were given two daily intravenous injections of 400 µL of normal human serum (NHS) or human serum that contained La-reactive autoantibodies (La serum). Mice were left intact or surgically castrated on the day that the first injection was given (column 2). Mice were killed for analysis two days after the second injection. High levels of hIgG cross-reactive with mouse La were detected by ELISA in all mice injected with La serum. The negative controls injected with NHS showed the same low background level of binding as non-injected normal mouse serum (NMS) (column 3). Hen egg lysozyme (HEL) was used as a negative control in the ELISA (column 4). Serum levels of hIgG were measured directly by quantitative ELISA and were found to be much higher than in the previously cited experiments (Tran et al, 2002b). Pregnant BALB/c mice were given injections of La serum and serum hIgG ranged from 0.01 to 0.4 g/L, which produced good opsonization of fetal apoptotic cardiomyocytes (column 5). The extent of prostate epithelial apoptosis was measured by TUNEL assay. Numbers indicated in the table represent TUNEL[+] nuclei detected in the prostatic epithelial layers that were available on whole sections. The numerous TUNEL[+] particles detected in the prostatic lumina of nearly all animals were not counted. There was a tendency toward increased apoptosis in the castrated mice in comparison to the intact mice (column 6). Binding of hIgG to apoptotic prostatic epithelial cells was detected in one of three mice, which was castrated and given an injection of La serum (column 7). In this case, numerous TUNEL[+] cells coated with bright particulate hIgG were detected in the prostatic lumen. Binding of hIgG to TUNEL[+] cells was seen also within the epithelium and on its surface. Immunolabeling of serial (adjacent) sections suggested the presence of both MHC-II[+] and F4/80[+] cells in the vicinity of these immunocomplexes (data not shown). Significantly, no binding of hIgG was detected in NHS-injected animals, or in La serum injected but non-castrated animals. As an additional control, ample background interstitial and intravascular hIgG was detected in all animals injected with either La serum or NHS (prostate, spleen, liver, salivary glands), which was in keeping with the detectable serum levels of hIgG. As expected, numerous apoptotic cells were detected in the spleen and thymus. In particular, the spleen showed significant speckle staining of hIgG (blood-tissue barrier being low in this tissue) without associated TUNEL staining. Apoptotic cells were barely detected in the salivary glands following castration, consistent with the notion that castration-induced apoptosis in glandular epithelium was prostate-specific.

TABLE 3

Tabulated and Narrative Summary of Experimental Results.

| Animal ID | Treatment | Serum hIgG bound to recombinant antigens (ELISA $OD_{405}$) | | Serum levels of hIgG (g/L) | TUNEL (+) nuclei in prostate epithelial layers per section | hIgG bound to apoptotic cells |
| --- | --- | --- | --- | --- | --- | --- |
| | | 6HismLa | 6HisHEL | | | |
| WT | Intact, La serum | 1.850 | 0 | 3.2 | 2, 3 | – |
| WT | Intact, La serum | 1.684 | 0 | 2.5 | 1 | – |
| WT | Castrated, La serum | 1.534 | 0 | 1.8 | >30 | + |
| WT | Castrated, La serum | 1.685 | 0 | 2.7 | 8, 10 | – |
| WT | Intact, NHS | 0.007 | 0 | 1.5 | N/A | – |
| WT | Castrated, NHS | 0.014 | 0 | 0.9 | 1, 3, 10 | – |
| TRAMP | Castrated, La serum | 1.588 | 0 | 2.4 | >30 | – |
| TRAMP | Intact, La serum | 1.389 | 0 | 1.6 | 5 | – |
| NMS | N/A | 0.016 | 0 | N/A | N/A | N/A |

EXAMPLE 2

Anti-LA Antibody Binds Apoptotic and Necrotic Cells

Figure 3:
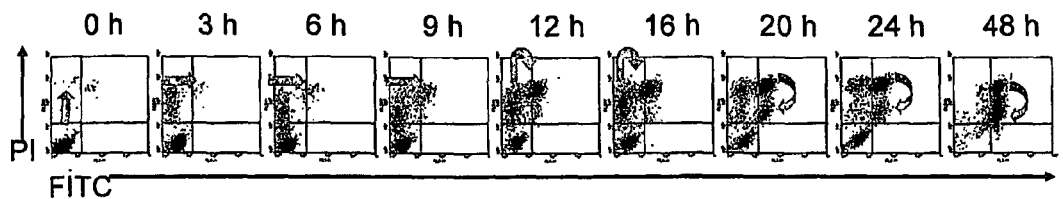
FIG. 3 is a graphical representation depicting that apoptotic bodies progressively form in vitro and bind anti-La antibody. Apoptosis was induced in the Jurkat human T cell leukemia cell line using 0.5 µM staurosporine (STS). Cells were stained with FITC-labelled 3B9 and the nuclear impermeant nucleic acid binding dye, propidium iodide (PI). The progressive formation of apoptotic bodies with time is indicated by arrows. Quadrant cursors are set for <3% staining with isotype control, Sal5.

As apoptosis is induced and progresses in vitro, apoptotic cells increasingly become leaky because of the loss of membrane integrity, which is manifest as increasing avidity for the nucleic acid and DNA binding dyes, propidium iodide (PI) and 7-amino-actinomycin D (7AAD), respectively. Binding of anti-La antibody to apoptotic cells has a slower time course than PI binding. However, the observed fluorescence intensity of anti-La antibody staining indicates that it binds with similar avidity to apoptotic cells irrespective of whether the PI staining is of high or intermediate intensity (FIG. 3). As is shown below, the $PI^{intermediate}$ subpopulation comprises apoptotic bodies. The intermediate staining does not result from quenching artefacts since it was present irrespective of changes in the concentration of PI.

Figure 2A:
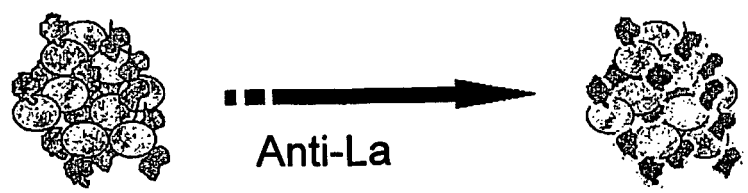
FIG. 2A shows that after the first chemotherapy, anti-La antibodies (yellow) detect apoptotic cancer cells (dark grey), which live close to viable cancer cells (light grey).
Figure 2B:
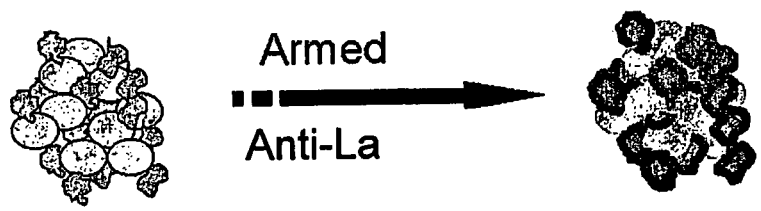
FIG. 2B shows that anti-La antibodies (purple), which are armed with a non-cross resistant anti-cancer treatment, deliver bystander killing to the remaining live cancer cells (red).

Accordingly, anti-La antibody binding to apoptotic cells is a function of the loss of membrane integrity as apoptosis proceeds in vitro. However, anti-La antibody binding to apoptotic cells is not simply a matter of passive binding of mAb because the fluorescence intensity of staining with Sal5, the isotype control mAb, was one log-fold lower than 3B9 (anti-monoclonal antibody) fluorescence intensity, which indicated that 3B9 bound specifically to its target antigen, human La/SS-B (upper and middle rows of panels, FIG. 4). While an anti-tubulin mAb, which recognises a component of the cytoskeleton, also demonstrated a high level of binding to apoptotic cells, it bound fewer $PI^{intermediate}$ apoptotic bodies (lower row of panels, FIG. 2) than 3B9 (46% of total PI+ events cf. 69%).

Figure 4:
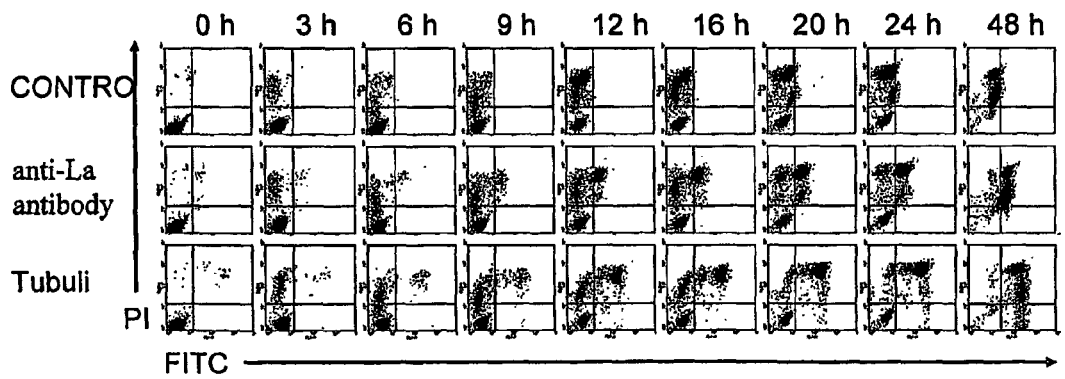
FIG. 4 is a graphical representation depicting that anti-La antibody binding to apoptotic Jurkat cells is associated with increasing membrane permeability. Apoptosis was induced to Jurkat cells using 0.5 µM STS. Cells were stained FITC-labelled Sal5 (isotype CONTROL) or FITC-labelled 3B9 (anti-La antibody) or FITC-labelled anti-β-tubulin mAb (Tubulin) and PI.
Figure 5:
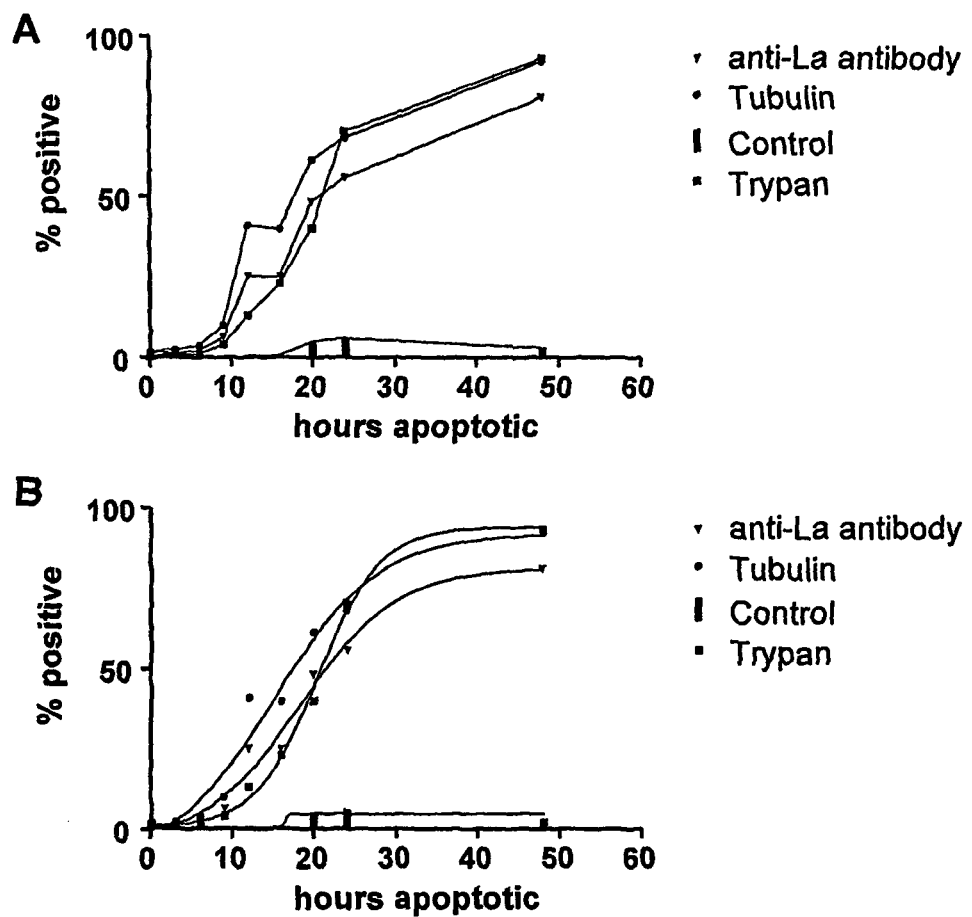
FIG. 5 is a graphical representation of the time course of anti-La antibody binding to apoptotic Jurkat cells. Apoptosis was induced in Jurkat cells using 0.5 µM STS. Cells were stained with FITC-labelled Sal 5 (isotype CONTROL) or FITC-labelled 3B9 (anti-La antibody) or FITC-labelled anti-β-tubulin mAb (Tubulin) trypan blue. The percentage of total cells at each time point that was positive for staining with each of these indicators is shown on the ordinate axis. Data are plotted as simple lines (A) or as fitted curves using a least squares method in Prism v3.0(B).

Some of the data shown in FIG. 4 are illustrated graphically and compared at each time point with the percentage of cells excluding trypan blue, which is another indicator of loss of cell viability (FIG. 5). It is clear that the kinetics of anti-La antibody binding to apoptotic cells parallels known markers of cell permeability (tubulin) and loss of cell viability (trypan blue), which supports the notion that the loss membrane integrity associated with apoptosis permits anti-La antibody binding.

Figure 6:
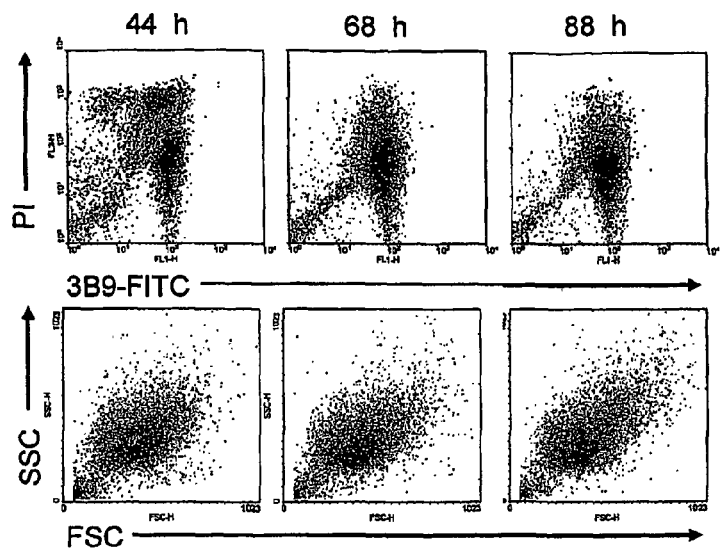
FIG. 6 is a graphical representation depicting that apoptotic bodies and anti-La antibody binding to apoptotic bodies is stable in vitro. Apoptosis was induced in Jurkat cells using 0.5 µM STS. Cells were stained with FITC-labelled 3B9 and propidium iodide (PI) (upper row). The size and internal complexity of the apoptotic bodies demonstrated using forward scatter (FSC) and side scatter (SSC), respectively (lower row).

As FIG. 6 illustrates, apoptotic bodies derived from apoptotic Jurkat cells were stable in size (lower row of panels, FIG. 6) with comparable intensity of staining for 3B9 (upper row of panels, FIG. 6) over a period that lasted for almost four days.

Figure 7:
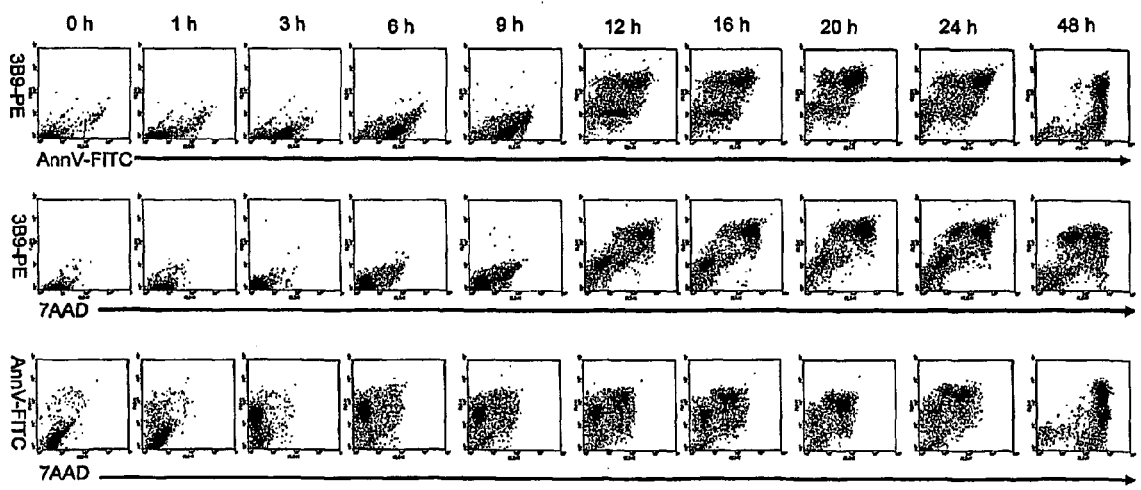
FIG. 7 is a graphical representation depicting that the binding of annexin V, 7AAD and anti-La antibody to apoptotic cells is interrelated and varies over time during apoptosis in vitro. Apoptosis was induced in Jurkat cells using 0.5 µM STS. Cells were stained with FITC-labelled human annexin V (annV-FITC), R-phycoerythrin-labelled 3B9 (PE-3B9) and 7AAD.
Figure 8:
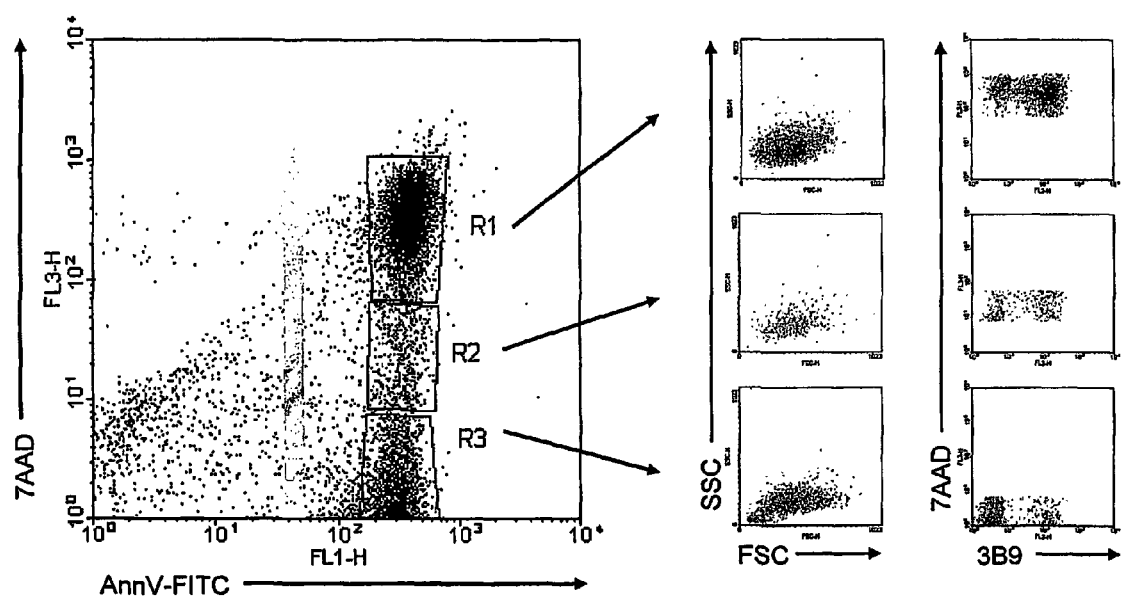
FIG. 8 is a graphical representation depicting that during apoptosis in vitro, the time-dependent binding of annexin V, 7AAD and anti-La antibody to apoptotic cells is interrelated. Apoptosis was induced in Jurkat cells using 0.5 µM STS. Cells were stained with FITC-labelled human annexin V (annV-FITC), R-phycoerthrin-labelled 3B9 (3B9) and 7AAD. Events in regions R1-3 (left hand panel) were analysed for size (forward scatter or FSC) and internal complexity (side scatter or SSC) (middle panels) and for staining with 7AAD and 3B9 (right hand panels).

Further kinetic analysis of anti-La antibody binding to apoptotic Jurkat cells was performed using annexin V to probe phosphatidylserine exposure on the outer plasma membrane, which is an early feature of apoptosis, and 7AAD to bind the DNA of leaky cells, which is a feature of late apoptosis. This analysis reveals again that anti-La antibody binding is commensurate with 7AAD binding but occurs later than annexin V binding (FIG. 7). This concept is displayed in another way in FIG. 8. anti-La antibody binding is insignificant during early apoptosis when cells are annexin V-positive but 7AAD-negative (R3 in left hand panel, FIG. 8) but anti-La antibody binding increases to high levels once the cells become permeable to 7AAD (R1 in left hand panel, FIG. 8).

Figure 9:
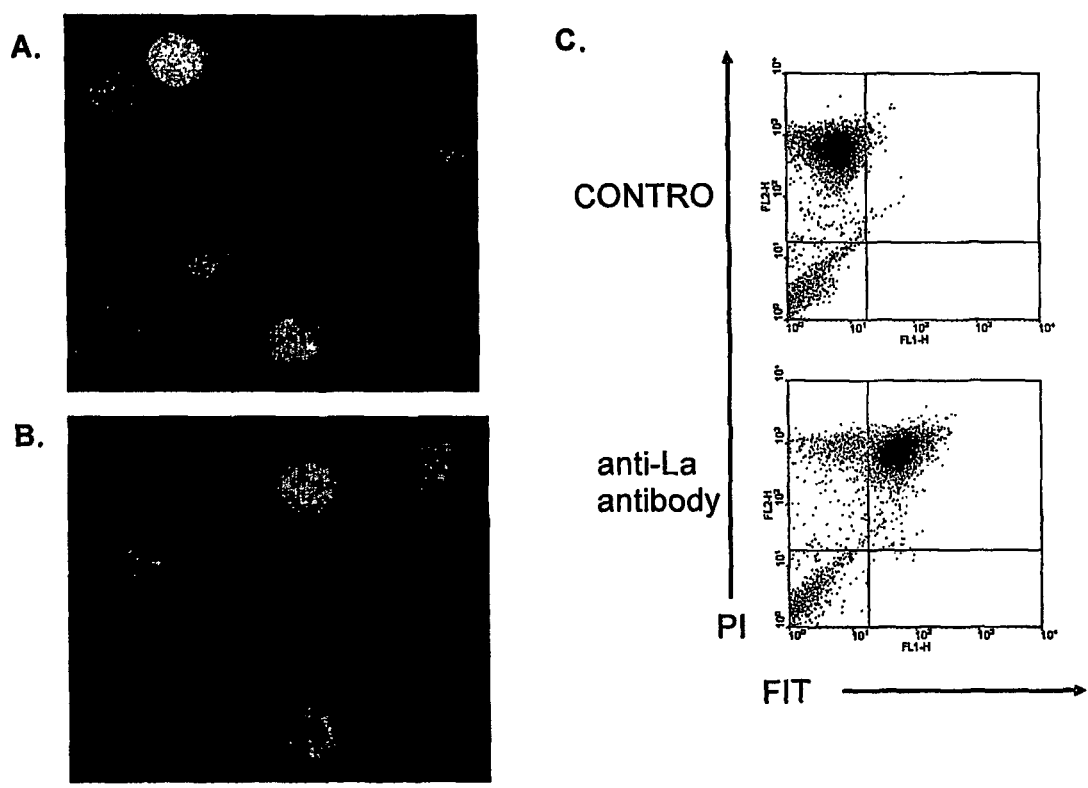
FIG. 9 comprises both an image and a graphical representation depicting that anti-La antibody binds to necrotic Jurkat cells. Necrosis was induced in Jurkat cells by heating at 56° C. for 1 hour. A. Cells were stained with Alexa488-labelled 3B9 (anti-La antibody) (green) and the nuclear impermeant DNA-binding dye, 7-amino-actinomycin D (7AAD) (red) or B. Alexa488-labelled 3B9 (anti-La antibody) (green) and R-phycoerthrin-labelled annexin V (red) and visualised by laser scanning confocal microscopy. C. Cells were stained with FITC-labelled Sal5 (isotype CONTROL) or FITC-labelled 3B9 (anti-La antibody) and PI and analysed by flow cytometry.

To emphasize that loss of cell membrane integrity is required for anti-La antibody binding, primary necrotic cells also demonstrate avid binding for anti-La antibody (FIG. 9). Note that anti-La antibody staining does not co-localise with DNA (FIG. 9A) or phosphatidylserine, which is exposed on necrotic cell membranes (FIG. 9B).

EXAMPLE 3

Anti-LA Antibody Binding to Apoptotic Bodies is Caspase 3 Dependent

Figure 10:
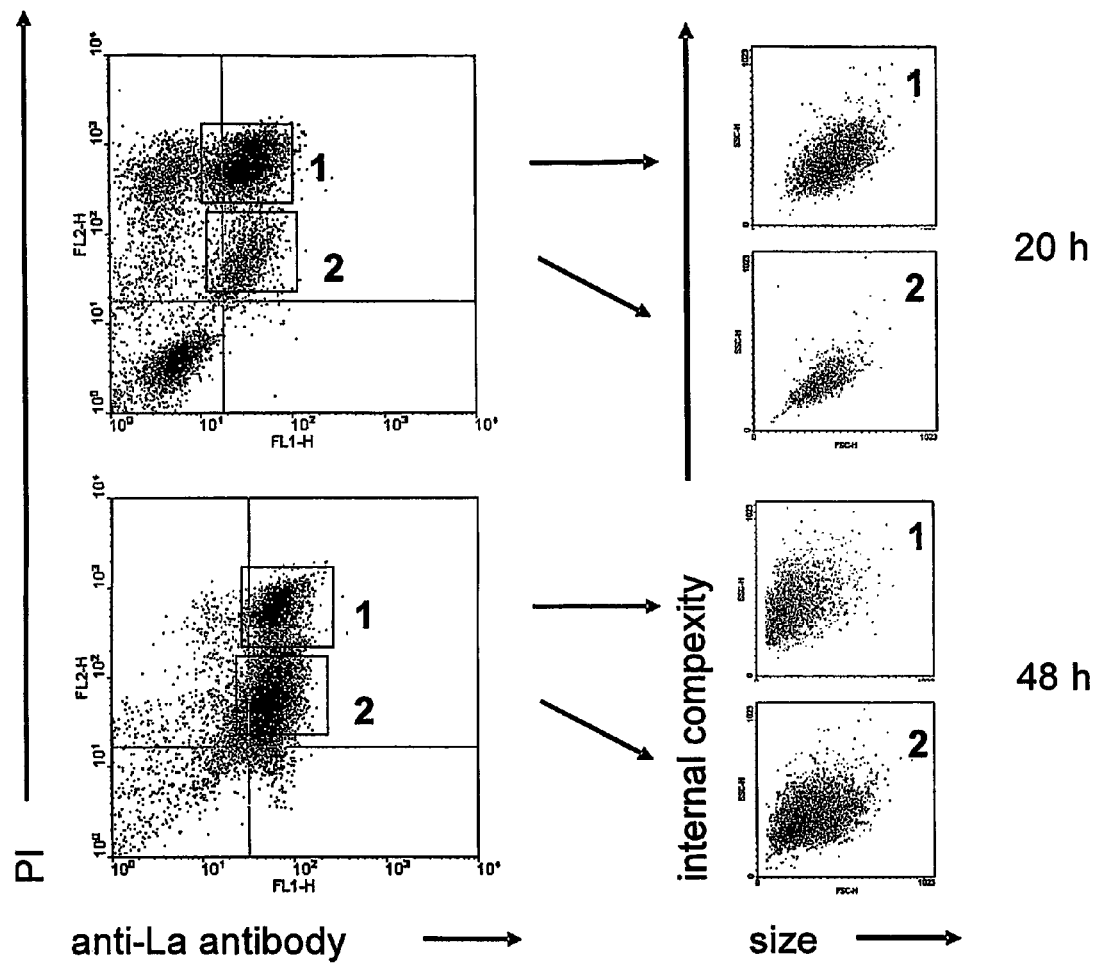
FIG. 10 is a graphical representation depicting that anti-La antibody preferentially binds late apoptotic cells and apoptotic bodies. Apoptosis was induced in Jurkat cells using 0.5 µM STS. Cells were stained with FITC-labelled 3B9 and PI. At 20 h or 48 h post-induction of apoptosis, 3B9$^+$ subpopulations that stained differentially with PI (1 and 2 in each left hand panel) were gated for analysis of scatter characteristics. Scatter analysis (right hand panels) shows that the 3B9$^+$ PI$^{in}_{termediate}$ events that accumulate with time are smaller (lower size as measured by forward scatter [FSC]) and less granular (reduced internal complexity as measured by forward scatter [SSC]) (lower right hand panel). Quadrant cursors are set for <3% staining with isotype control, Sal5.

As mentioned in Example 2, more detailed flow cytometric analysis indicated that anti-La antibody bound apoptotic bodies, which are characterized by their smaller size and reduced internal complexity because they contain varying proportions of membrane-bound remnants of nuclear components and cellular organelles (FIG. 10). Furthermore, it is shown that apoptotic body formation is a requirement for anti-La antibody binding. MCF-7 is a human breast cancer cell line that lacks the gene for pro-caspase 3.

Pro-caspase 3 is a pro-enzyme form of the crucial executioner caspase, caspase 3, which catalyses the cleavage of many functional and structural proteins in the dying cell.

Caspase 3-mediated cleavage of these proteins contributes to the morphological appearances of apoptotic body formation, which is the splitting of the apoptotic cell into several (or more) smaller membrane-bound parcels known as apoptotic bodies. Although MCF-7 cells do not demonstrate apoptotic body formation during cell death, this phenotype can be rescued by the transfection of the gene for pro-caspase 3 into MCF-7 cells.

As illustrated in FIG. 10, transient transfection of MCF-7 cells with the gene for pro-caspase 3 generates apoptotic bodies and consequent binding of anti-La antibody. Hence, anti-La antibody binding to apoptotic bodies is caspase 3 dependent. These apoptotic bodies did not stain with 7AAD, which preferentially stains DNA rather than RNA (lower left hand panel, FIG. 10). Moreover, when evaluated by scatter criteria, apoptotic bodies were smaller in size (lower right hand panel, FIG. 10).

Figure 11:
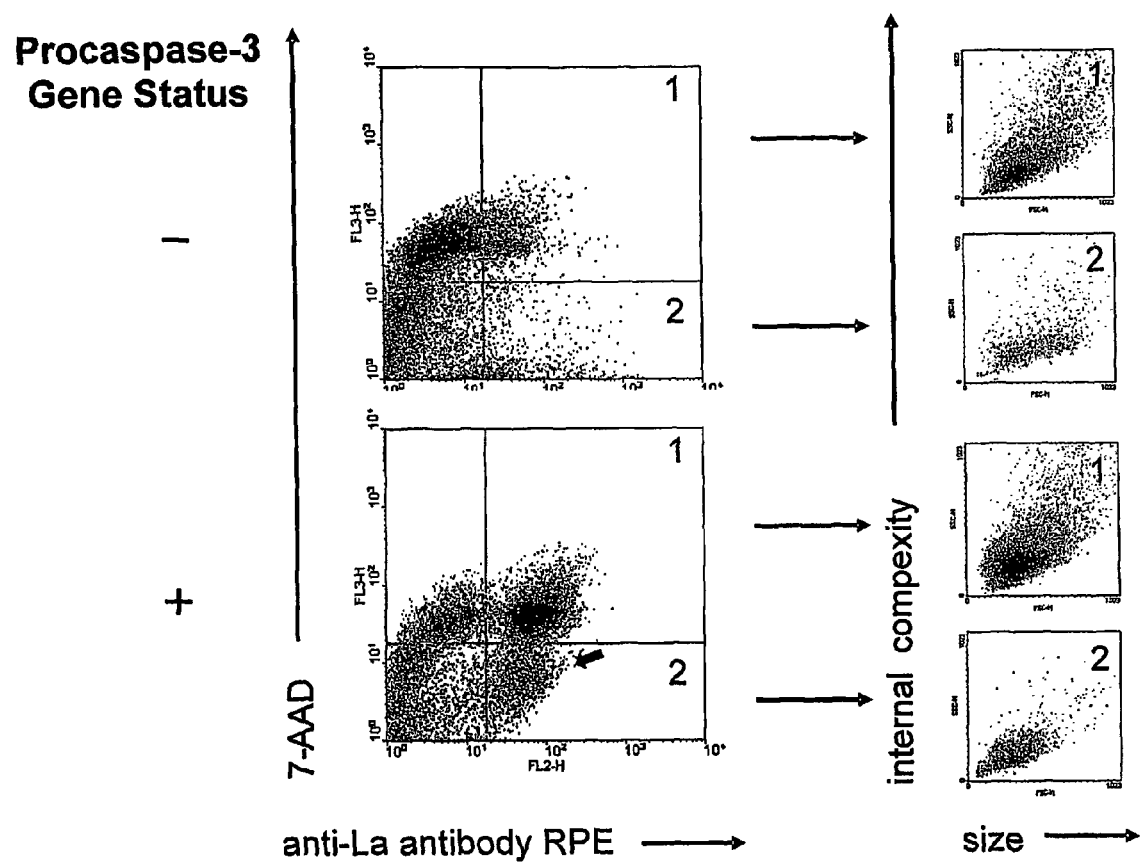
FIG. 11 is a graphical representation depicting that anti-La antibody binding is caspase 3 dependent and associated with apoptotic body formation. MCF-7 cells were transiently transfected with plasmid DNA vectors that expressed enhanced green fluorescent protein (EGFP) alone or pro-caspase 3 and EGFP. Apoptosis was induced in the transiently transfected MCF-7 cells using 0.5 µM STS and the cells were stained with FITC-labelled 3B9 and 7AAD. The cells shown in the scatter plots (left hand panels) had been gated on green fluorescence. Subsequently, events in quadrants 1 and 2 of each scatter plot (left hand panels) had been gated for analysis of scatter characteristics. Scatter analysis (right hand panels) shows that 3B9 binding is caspase 3 dependent and hence associated with apoptotic body formation because apoptotic bodies were smaller (lower size as measured by forward scatter [FSC]) and less granular (reduced internal complexity as measured by forward scatter [SSC]) (lower right hand panels). Quadrant cursors are set for <3% staining with isotype control, Sal5.

Next, MCF-7 cells that had been stably transfected with the gene for pro-caspase 3 were studied. As in FIG. 11, MCF-7 cells that contained the control vector or the pro-caspase 3 gene were rendered apoptotic and stained with 3B9 that had been labelled with the green fluorochrome, Alexa488 and propidium iodide (FIG. 11A). Again, caspase 3 activity was shown to be required for anti-La antibody binding to apoptotic bodies. Fluorescence microscopy of these cells demonstrated that pro-caspase 3 expressing MCF-7 transfectants had budded and partitioned distinctly 3B9$^+$ apoptotic bodies (FIG. 11C). On the other hand, vector control MCF-7 cells showed a less discrete pattern of 3B9 staining (FIG. 11C), which is consistent with the broad distribution of 3B9 staining observed by flow cytometry in vector control MCF-7 cells (upper right hand panel, FIG. 11A). In contrast, as in FIG. 10, caspase 3 activity conferred a restricted pattern of 3B9 staining (lower right hand panel, FIG. 11A), which suggested that the activity of caspase 3 had resulted in uniform partitioning of La/SS-B antigen among apoptotic bodies.

Figure 12:
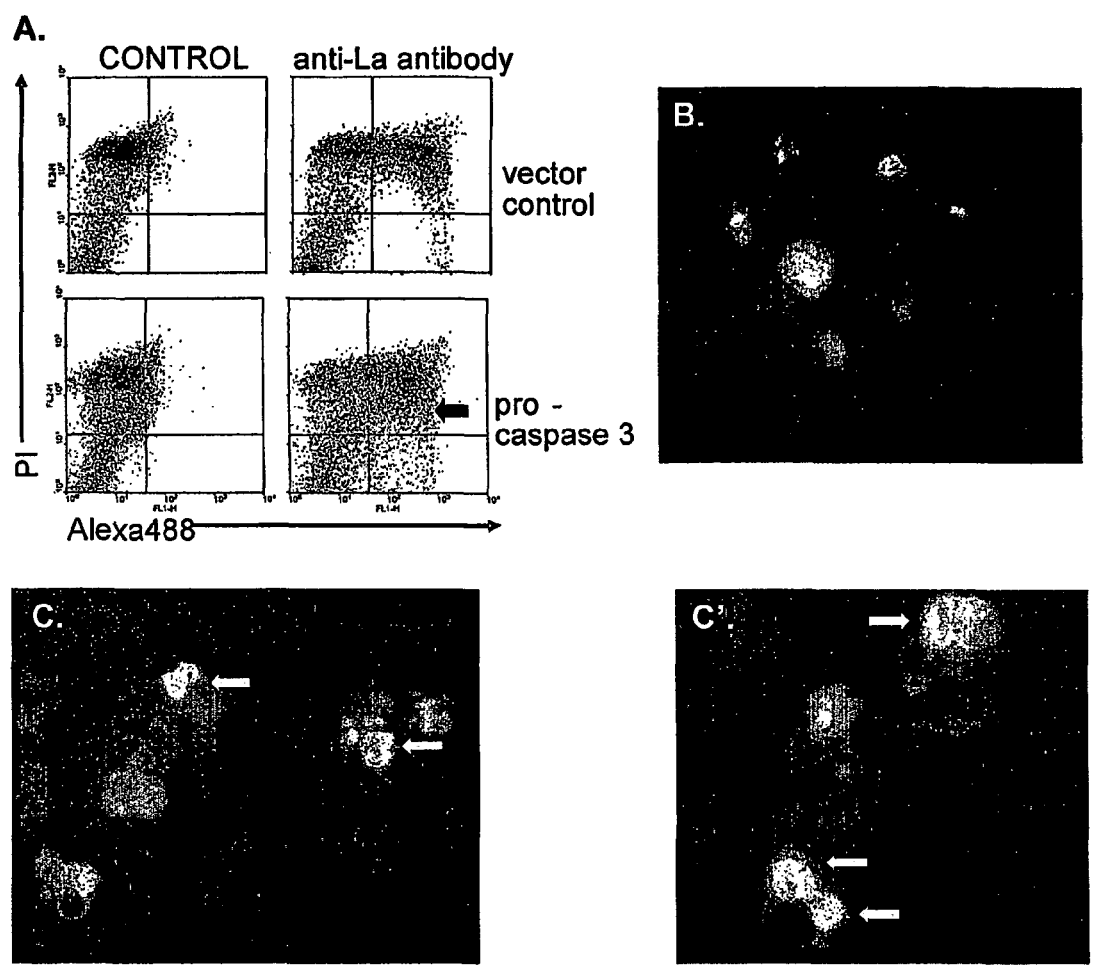
FIG. 12 comprises both an image and a graphical representation depicting that anti-La antibody binding is caspase 3 dependent and associated with apoptotic body formation. MCF-7 cells were stably transfected with either a vector control (B) or a vector that expressed pro-caspase 3 (C and C'). MCF-7 transfectants were rendered apoptotic by 24 h treatment with 1 µM STS. A. For flow cytometry, cells were stained with Alexa488-labelled 3B9 and propidium iodide (PI). B, C and C'. For fluorescence microscopy, cells were stained with Alexa488-labelled 3B9 (green) and the nuclear dye DAPI (blue). Apoptotic bodies are indicated (arrows).
Figure 13:
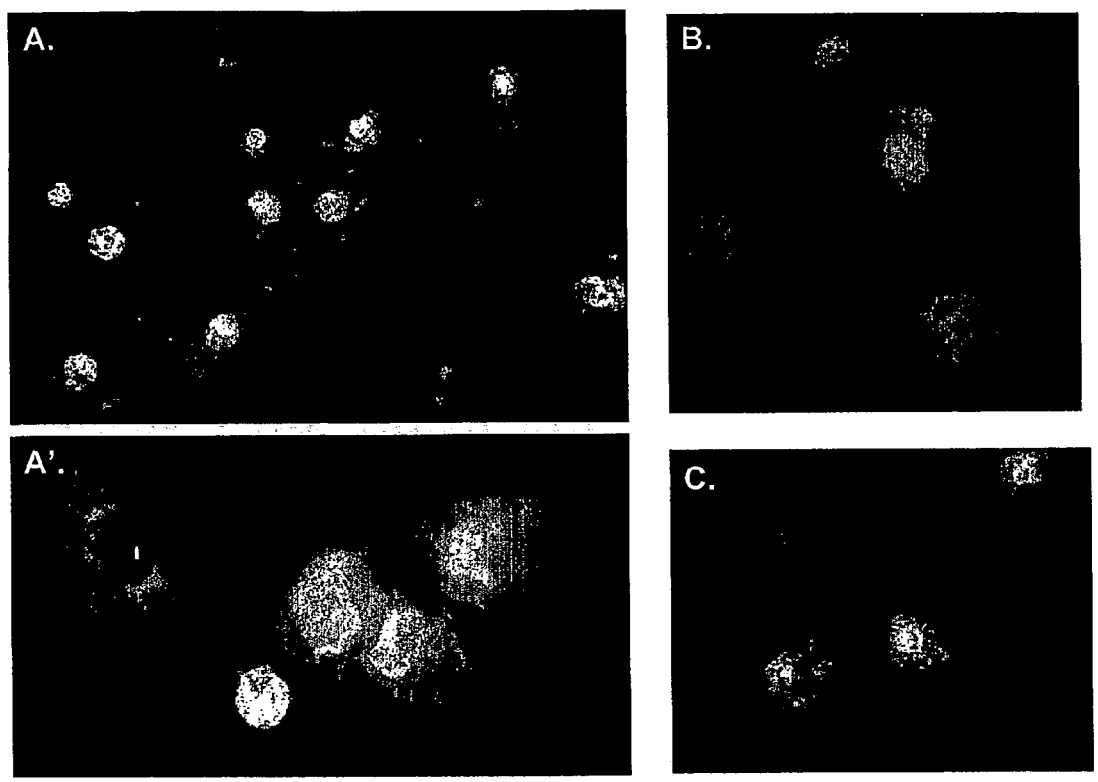
FIG. 13 is an image of anti-La antibody loading the cytoplasm of dead cells. Apoptosis was induced in Jurkat cells by 24 h treatment with 0.5 µM STS. Cells were stained with the nuclear impermeant dye TOPRO3 (blue), Alexa488-labelled 3B9 or anti-La antibody, the isotype control Sal 5 or anti-PARP mAb (green) and R-phycoerythrin (PE)-labelled human annexin V (red) and viewed using confocal laser scanning microscopy. A. lower and A'. higher magnifications are shown for Alexa488-labelled 3B9 staining; B. negative isotype control staining for anti-La antibody using Sal5; C. anti-PARP staining.

As illustrated in FIG. 12, confocal laser scanning microscopy of apoptotic Jurkat cells was used to show that anti-La antibody staining neither overlapped with staining for apoptotic cell membranes that had everted phosphatidylserine (as detected by annexin V) nor staining for DNA (as detected by TOPRO3) (FIG. 13A). Moreover, serial vertical-sections confirmed that anti-La antibody staining occurred throughout the cytoplasmic region of dead cells. This staining with 3B9 was specific because barely any staining was observed using the isotype control mAb, Sal5 (FIG. 13B). PARP, which is an abundant nuclear antigen (comprising approximately 2% of nuclear protein) and which is also cleaved by caspase 3 during apoptosis, adopted a similar pattern of staining to 3B9 when detected with a specific mAb (FIG. 12C). Together, these data suggested that anti-La antibody 'loads' the cytoplasm of dead cells (FIG. 13).

Figure 14:
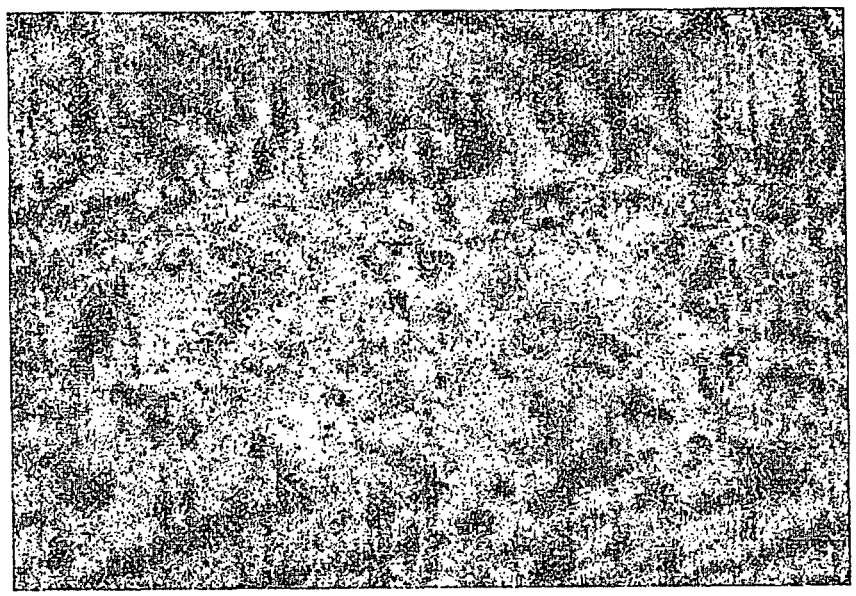
FIG. 14 is an image depicting that other monoclonal antibodies directed against other nuclear and ribonuclear antigens also bind apoptotic bodies. Apoptosis was induced in Jurkat cells by a 24 h treatment with 0.5 µM STS. Cells were stained with Alexa488-labelled anti-α-fodrin mAb (green) and 7AAD (red) and visualised by laser scanning confocal microscopy.

Other mAb specific for nuclear antigens such as Fodrin, which is also cleaved by caspase 3 and thus contributes to apoptotic body formation, stain apoptotic Jurkat cells with a staining pattern that is similar to that exhibited by 3B9 (FIG. 14). Similar patterns of staining were also observed for mAb, which are specific for PCNA and lamin B. These mAb demonstrated widespread cytoplasmic staining that did not co-localise with DNA as detected by 7AAD. Indeed, 7AAD tended to be restricted to peripheral apoptotic blebs. In contrast, staining with anti-β-tubulin mAb was evident throughout apoptotic cells where it co-localised to some extent with 7AAD staining.

Figure 15:
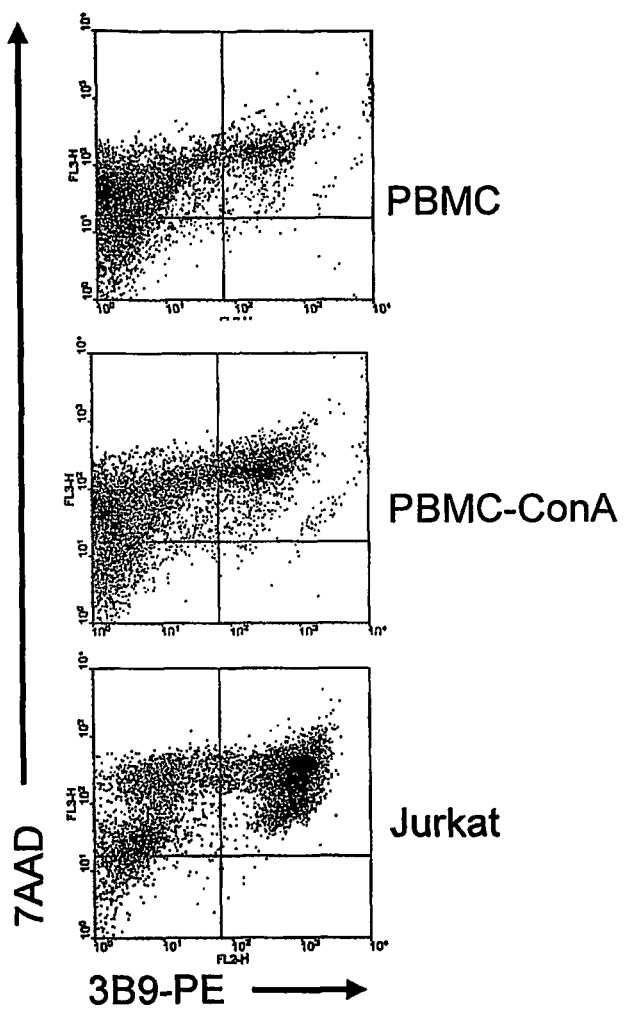
FIG. 15 is a graphical representation depicting that La/SS-B expression is up-regulated after apoptosis of malignant Jurkat T cells in comparison with apoptotic primary T cells. Ficoll-purified peripheral blood mononuclear cells (PBMC) were cultured for 4 d in RPMI-1640 with 10% fetal calf serum and then treated with 1 µM STS in the final 24 h of culture. Similarly, PBMC were activated with the T cell mitogen conconavalin A (PBMC-ConA) 10 µg/mL for 4 d before apoptosis was induced with 1 µM STS in the final 24 h of culture. Jurkat cells (Jurkat) were rendered apoptotic by 24 h treatment with 0.5 µM STS. Quadrant cursors are set for <3% staining with isotype control, Sal5.

Anti-La antibody also binds apoptotic primary T cells, which comprise the majority of peripheral blood mononuclear cells (PMBC). However, the fluorescence intensity of anti-La antibody binding to primary T cells is approximately one half-log fold less than that observed for malignant Jurkat T cells even if the PBMC had previously been activated with the T cell mitogen, conconavalin A (FIG. 15).

EXAMPLE 4

Figure 16:
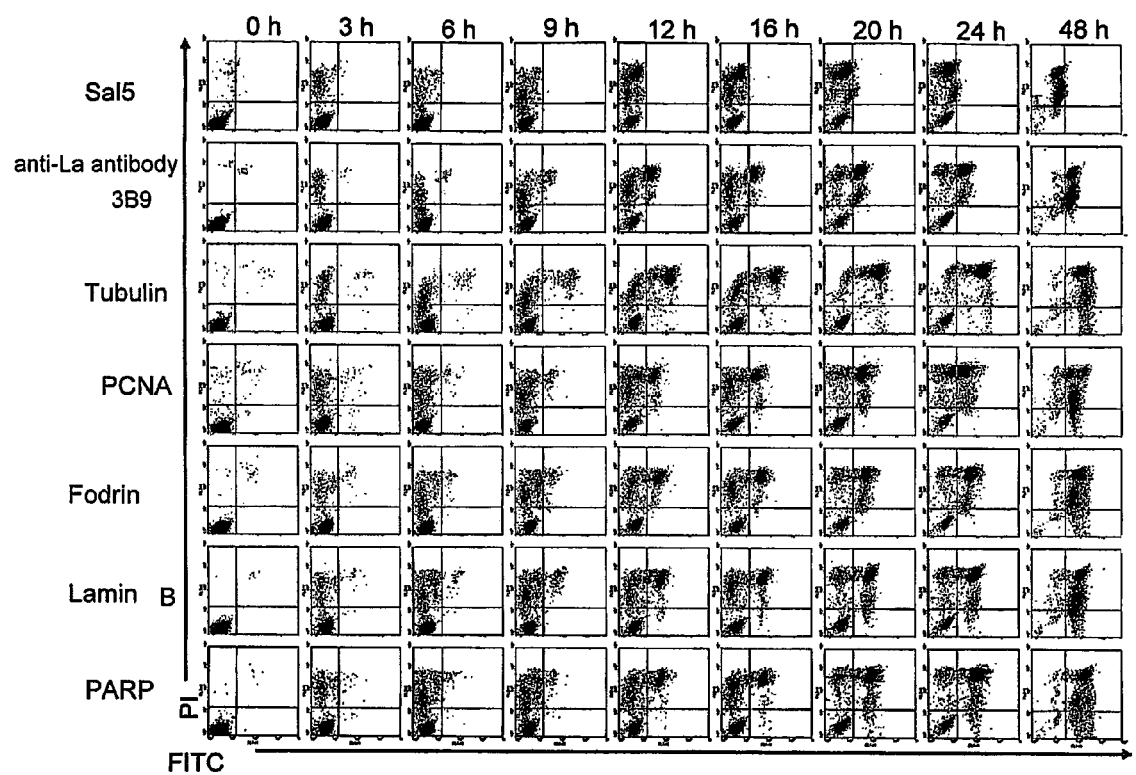
FIG. 16 is a graphical representation depicting that other monoclonal antibodies directed again other nuclear and ribonuclear antigens also bind apoptotic cells. Apoptosis was induced in Jurkat cells using 0.5 µM STS. Cells were stained with PI and various FITC-labelled mAb: isotype control, Sal5, for anti-La/SS-B clone 3B9 (anti-La antibody), anti-β-tubulin clone TUB2.1 FITC conjugate (Sigma F 2043), Proliferating Cell Nuclear Antigen (PCNA) Clone PC10 (Oncogene Cat#NA03), mouse anti-α-fodrin (nonerythroid anti-spectrin) Chemicon MAB1622, anti-lamen B Clone 101-B7 (Oncogene cat#NA12) and anti-PARP clone C2-10 (Oncogene cat# AM30). Quadrant cursors are set for <3% staining with correspondence isotype control antibodies.
Figure 17:
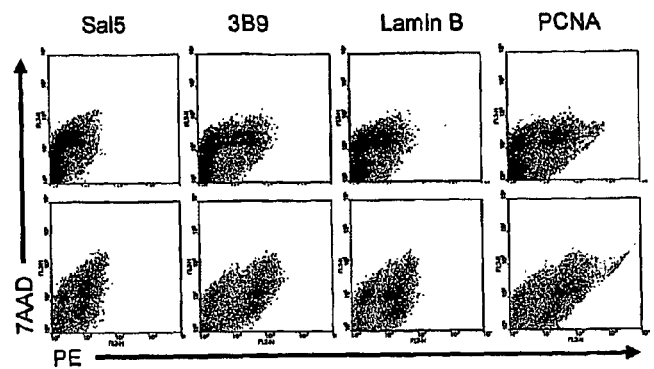
FIG. 17 is a graphical representative depicting that other monoclonal antibodies directed against other nuclear and ribonuclear antigens also bind apoptotic bodies. MCF-7 cells were transiently transfected with plasmid DNA vectors that expressed EGFP alone or pro-caspase 3 and EGFP. Apoptosis was induced in the transiently transfected MCF-7 cells using 0.5 µM STS and the cells were stained with 7AAD and FITC-labelled isotype mAb, Sal5, and mAb directed against La/SS-B (3B9), lamin B and Proliferating Cell Nuclear Antigen (PCNA). Upper row of panels show non-transfected MCF-7 cells (gated as EGFP-positive). The appearances of the non-transfected MCF-7 cells are nearly identical to those of MCF-7 cells that had been transfected with the DNA vector that expressed EGFP alone (data not shown).

Other Monoclonal Antibodies Directed Against Other Nuclear and Ribonuclear Antigens also Bind Apoptotic Cells As observed in confocal scanning laser microscopy studies, flow cytometry shows similar kinetics and patterns of binding of a number of mAb, which are specific for nuclear and ribonuclear antigens. Anti-tubulin mAb is included as a control for cytoplasmic binding in permeable apoptotic cells (FIG. 16). Similarly, some of these mAb specifically bind apoptotic bodies that form after MCF-7 cells have been transfected with the gene for pro-caspase 3 (FIG. 17).

EXAMPLE 5

Other Antibodies Directed Against Human La/SS-B also Detect Apoptotic Cells

Figure 18:
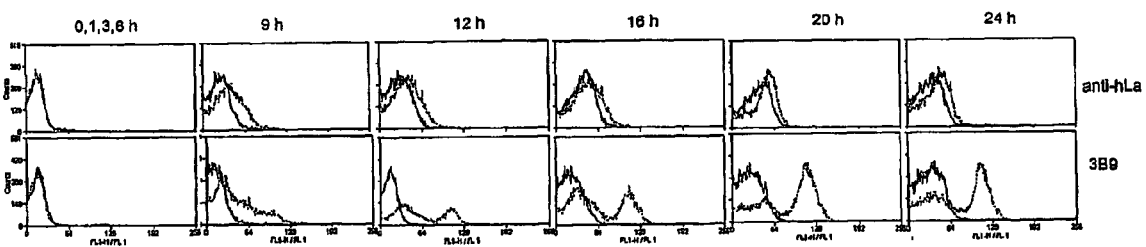
FIG. 18 is a graphical representation depicting that apoptotic human cells are detected by human anti-La autoantibodies. Jurkat cells that had been rendered apoptotic by treatment with 0.5 µM STS were stained with human anti-La autoantibodies that had been La-affinity purified (upper row of panels) or murine mAb 3B9 directed against human La (lower row of panels). PI+ cells were gated and data are presented as histograms for each time point after apoptosis induction. Negative control, human IgG (thick line); human anti-hLa antibodies and 3B9 (thin line).
Figure 19:
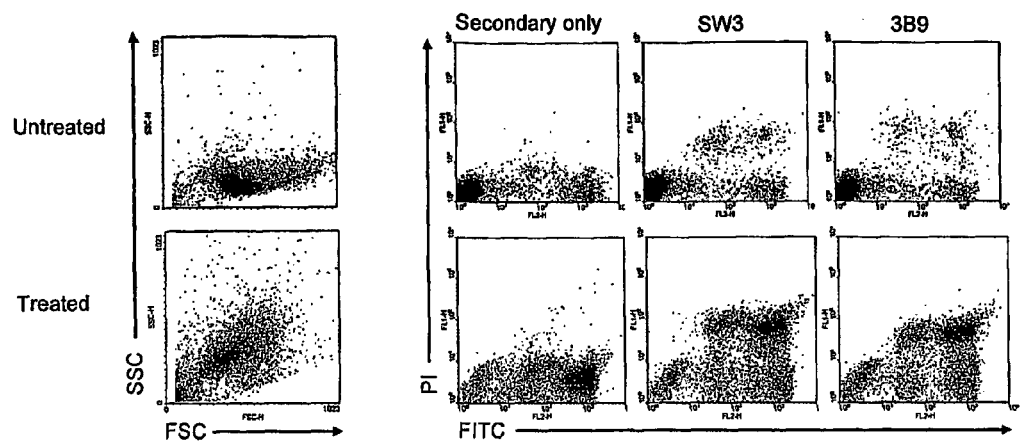
FIG. 19 is a graphical representation depicting that apoptotic human cells were also detected by another anti-human La/SS-B monoclonal antibody. Jurkat cells were either left untreated in culture in vitro (Untreated) or treated with 0.5 µM STS for 17 h to induce apoptosis (Treated). Cells were stained with PI and FITC-labelled anti-murine secondary antibody or mAb clone SW3 or mAb clone 3B9.

Binding to apoptotic cells of human anti-La autoantibodies (FIG. 18) and another mAb, clone SW3, which is specific for human La/SS-B (FIG. 19) was studied.

EXAMPLE 6

Figure 20:
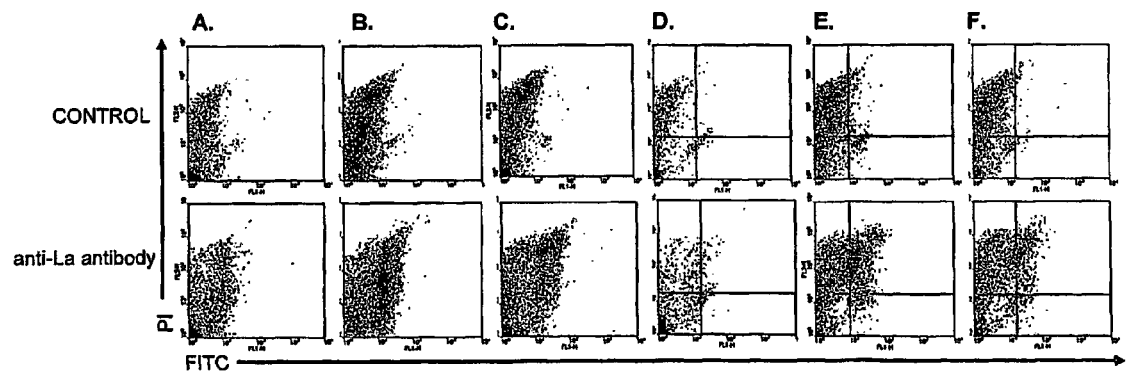
FIG. 20 is a graphical representation depicting that anti-La antibody binds primary apoptotic cells from rodent species. Murine (A-C) or rat (D-F) thymocytes were cultured in vitro for 21-24 h without supplements (A, D), or with the addition of 1 µM dexamethasone (B, E) or 0.5 µM STS (C, F). Cells were stained with FITC-labelled isotype mAb, Sal5 (CONTROL) or FITC-labelled 3B9 (anti-La antibody) and propidium iodide (PI).
Figure 21:
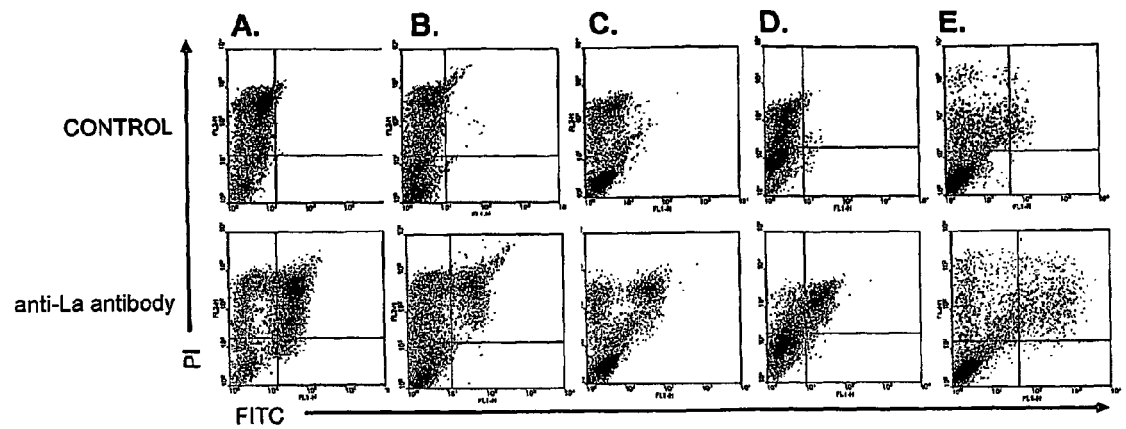
FIG. 21 is a graphical representation depicting that anti-La antibody binds apoptotic tumour cells from rodent species. The murine thymic lymphoblastic cell line, EL-4 (A-E) or the rat prostrate cancer cell line, AT-3.1 (F) were cultured in vitro (A-C, F) for 24 h with 0.5 µM STS (A, F), etoposide (B) or etoposide and cyclophosphamide (C), or EL-4 tumour cells were recovered from subcutaneous implants in syngeneic C57BL/6 mice, which had been left untreated (D) or treated in vivo with cyclophosphamide and etoposide for 48 h to induce tumour apoptosis (E). Cells were stained with FITC-labelled isotype mAb, Sal5 (CONTROL) or FITC-labelled 3B9 (anti-La antibody) and propidium iodide (PI).
Figure 22:
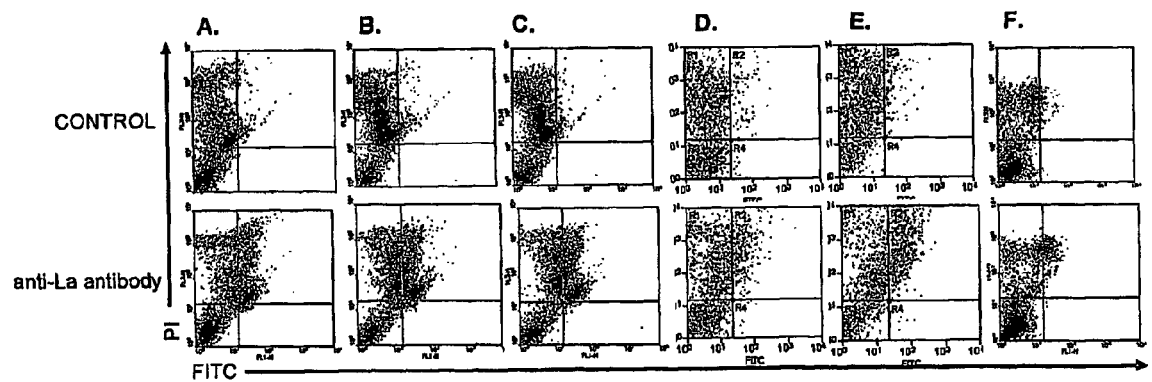
FIG. 22 is a graphical representation depicting that anti-La antibody binds a number of apoptotic human and monkey tumour cell lines. The cell lines were treated with 0.5-1 µM STS for 24 h to induce apoptosis: A. Jurkat T cell leukemia; B. U2OS osteosarcoma cells; C. HeLa cervical cancer cells; D. MG63 osteosarcoma cells; E. COS-7 monkey kidney fibroblastic cells. Cells were stained with FITC-labelled isotype mAb, Sal (CONTROL) or FITC-labelled 3B9 (anti-La antibody) and propidium iodide (P).
Figure 23:
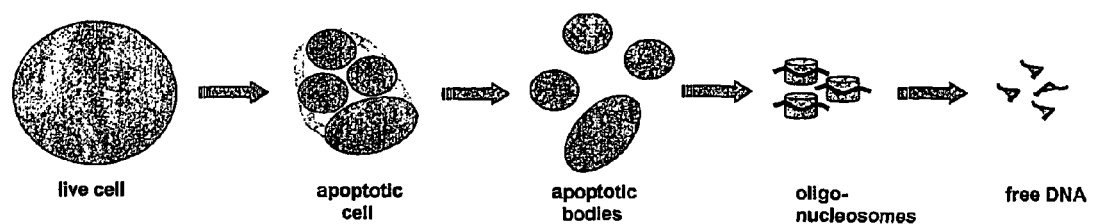
FIG. 23 is a schematic depiction of the progression of apoptosis through various stages in vitro. After an apoptotic stimulus, apoptotic cells shrink and fragment into membrane bound parcels known as apoptotic bodies that become increasingly leaky or secondarily necrotic with time. Eventually the apoptotic bodies disintegrate to oligonucleosomes and then free DNA.
Figure 24:
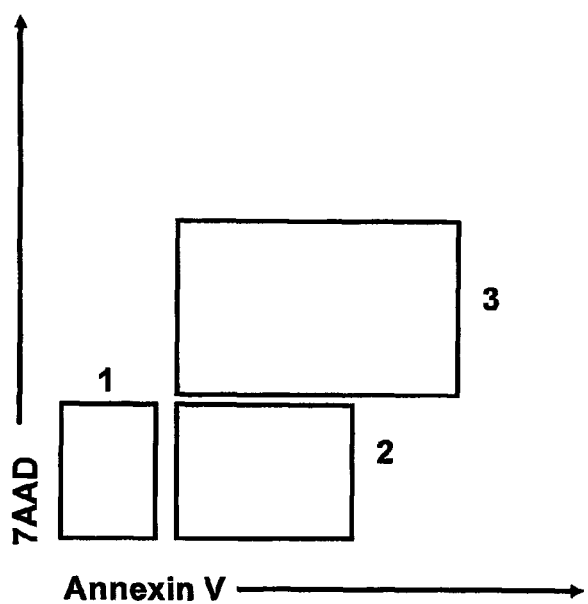
FIG. 24 is a graphical depiction of the stage of apoptosis is conventionally defined by staining with annexin V and nuclear impermeant dyes such as 7AAD. Jurkat cells were rendered apoptotic with 0.5 µM staurosporine for 16 h and stained with annexin V (AV) and 7-amino-actinomycin D (7AAD). 1, viable cells (AV$^-$, 7AAD$^-$); 2, early apoptotic cells (AV$^+$, 7AAD$^-$); 3, late apoptotic cells (AV$^+$, 7AAD$^+$).

Anti-La Antibody Binds Primary and Malignant Apoptotic Cells from Human and Rodent Species In addition to the binding of apoptotic primary human cells (FIG. 15), anti-La antibody also binds apoptotic primary cells from the thymi of mice and rats in which apoptosis was induced in vitro with dexamethasone or staurosporine. Anti-La antibody specifically binds PI$^+$ thymocytes in response to apoptosis that was induced with either stimulus (FIG. 20). A similar pattern of binding was observed using a mAb directed against proliferating cell nuclear antigen (PCNA). Anti-La antibody also binds apoptotic tumour cells from rodent species (FIG. 21), which includes tumour cells that have undergone apoptosis in vivo in response to cytotoxic drugs, together with a number of apoptotic human and monkey tumour cell lines (FIG. 22).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Adams et al., *Cancer Res.* 53: 4026-4034, 1993.
Bachmann et al. *Proc Natl Acad Sci USA* 83 (20):7770-7774, 1986
Blankenberg et al. *Clin Cancer Res* 2002
Brinkley et al., U.S. Pat. No. 5,326,692.
Callahan et al. *Cell Death Different* 7(7):645-653, 2000
Carmo-Fonseca et al. *Exp Cell Res* 185(1):73-85, 1989
Chothia et al., *J. Mol. Biol.* 196: 901, 1987.
Chothia et al., *J. Mol. Biol.* 227: 799, 1992.

Chou et al. (U.S. Pat. No. 6,056,957).
Coligan et al., *Current Protocols in Immunology*, John Wiley & Sons, Inc., 1991-1997.
Cumber et al., *J. Immunol.* 149: 120-126, 1992.
Davies & Riechmann, *FEBS Lett.* 339: 285-290, 1994.
Gefter et al., *Somatic Cell Genet.* 3: 231-236, 1977.
Glockshuber et al., *Biochem.* 29: 1363-1367, 1990.
H. Lecoeur et al. *J Immunol Methods* 2002.
Hamel et al. *Cytometry* 25(2):173-181, 1996.
Hamers-Casterman et al., *Nature* 363: 446-448, 1993.
Jones et al., *Nature* 321: 522-525, 1986.
Kabat et al., "*Sequences of Proteins of Immunological Interest*", U.S. Department of Health and Human Services, 1983.
Kennet et al. (eds) *Monoclonal Antibodies and Hybridomas: A New Dimension in Biological Analyses*, pp. 376-384, Plenum Press, New York, 1980.
Kohler and Milstein, *Eur. J. Immunol.* 6(7): 511-519, 1976.
Kohler and Milstein, *Nature* 256: 495-499, 1975.
Kostelny et al., *J. Immunol.* 148: 1547-1553, 1992.
Kozbor et al., *Methods in Enzymology* 121: 140, 1986.
Krahlung et al. *Cell Death Different* 6(2):183-189, 1999.
Krebber et al., *J. Immunol. Methods* 201(1): 35-55, 1997.
Ku & Schutz, *Proc. Natl. Acad. Sci. USA* 92: 6552-6556, 1995.
Liu et al., *Proc. Natl. Acad. Sci. USA* 84: 3439-3443, 1987.
Mamula et al. *J Immunol* 143(9):2923-2928, 1989.
Morgan et al. (U.S. Pat. No. 6,180,377).
Morikawa et al. *Cancer Immunol Immunother* 27(1):1-6, 1988.
P. Smolewski et al. *J Immunol Methods* 2002.
Plückthun et al., *In Antibody engineering: A practical approach* 203-252, 1996.
Plünckthun, *Biochem.* 31: 1579-1584, 1992.
Pruijn et al. *Eur J Biochem* 232(2):611-619, 1995.
Queen et al. (U.S. Pat. No. 6,180,370).
Ravirajan et al. *Lupus* 1(3):157-165, 1992.
Reiter et al., *Biochem.* 33: 5451-5459, 1994.
Reiter et al., *Cancer Res.* 54: 2714-2718, 1994.
Reiter et al., *J. Biol. Chem.* 269: 18327-18331, 1994.
Richmann et al., *Nature* 332: 323-327, 1988.
Shinohara et al. *J Immunother* 23(3):321-331, 2000.
Shulman et al., *Nature* 276: 269-270, 1978.
Singer et al., U.S. Pat. No. 5,573,909.
Toyama et al., "*Monoclonal Antibody, Experiment Manual*", published by Kodansha Scientific, 1987.
Tran et al. *Arthritis Rheum* 46(1):202-208, 2002.
Troster et al. *J Autoimmunity* 8(6):825-842, 1995.
Trowbridge, *J. Exp. Med.* 148(1): 313-323, 1978.
Verhoeyen et al., *Science* 239: 1534-1536, 1988.
Volk et al., *J. Virol.* 42(1): 220-227, 1982.
Ward et al., *Nature* 341: 544-546, 1989.
Webber et al., *Mol. Immunol.* 32: 249-258, 1995.
Winter and Milstein, *Nature* 349: 293, 1991.
Wu et al. *Nature Biotechnol* 2002.

The invention claimed is:

1. A method of treating a neoplastic condition in a subject, comprising:
administering to said subject an effective amount of an immunointeractive molecule which binds to La-SS/B or antigenic determinant or epitope thereof, wherein said immunointeractive molecule is an antibody, a monoclonal antibody, a polyclonal antibody, a humanized antibody, a chimaeric antibody, a minibody, a single chain antibody, a deimmunised antibody, an Fv fragment, an Fab fragment, an Fab' fragment, an F(ab')$_2$ fragment, an (scFv-Fc)$_2$ fragment, a single chain Fv fragment, a disulphide-stabilised Fv fragment or a single variable region domain (dAb), and wherein said immunointeractive molecule is linked, bound or otherwise associated with a proteinaceous or non-proteinaceous molecule which downregulates growth of tumor cells, for a time and under conditions sufficient to treat said neoplastic condition.

2. The method according to claim 1, wherein said neoplastic condition is a central nervous system tumour, retinoblastoma, neuroblastoma or other paediatric tumour, head and neck cancer, breast and prostrate cancer, lung cancer, kidney cancer, oesophagogastric cancer, hepatocellular carcinoma, pancreaticobiliary neoplasia, colorectal cancer, cervical or anal cancer, uterine or other reproductive tract cancer, urinary tract cancer, germ cell tumour, ovarian cancer, carcinoma of unknown primary, human immunodeficiency associated malignancy, lymphoma, leukemia, malignant melanoma, sarcoma, endocrine tumour, mesothelioma or other pleural tumour, neuroendocrine tumour, or carcinoid tumour.

3. The method according to claim 2, wherein said head and neck cancer is a squamous cell cancer, said lung cancer is a small or non-small lung cell cancer, said kidney cancer is a renal cell adenocarcinoma, said pancreatic reoplasma is an adenocarcinoma islet cell tumour, said germ cell tumour is testicular cancer or ovarian cancer, said ovarian cancer is an ovarian epithelial cancer, said human immunodeficiency associated malignancies is kaposis sarcoma, and said endocrine tumour is a tumour of the thyroid gland.

4. The method according to claim 2, wherein said neoplasm is metastatic cancer.

5. The method according to claim 1, wherein said condition is a tumour and wherein said proteinaceous or non-proteinaceous molecule is selected from the group consisting of:
 (a) a cytokine;
 (b) a chemokine;
 (c) a macrophage, dendritic cell or T cell activator; and
 (d) a toxin.

6. The method according to claim 5, wherein said macrophage activator is N-formyl-methionyl-leucyl-phenylalanine or a bacterial lipopeptide.

7. The method according to claim 6, wherein said bacterial lipopeptide is JBT2002.

8. The method according to claim 5, wherein said toxin is a radioisotope.

9. The method according to claim 8, wherein said radioisotope is an alpha particle emitter, a beta particle emitter or a gamma particle emitter.

10. The method according to claim 9, wherein said alpha emitter is Tb-149 or Bi-213.

11. The method according to claim 5, wherein said toxin is ricin, a prodrug or a biotherapeutic agent.

12. The method according to claim 11, wherein said prodrug is an antibody-directed prodrug converting enzyme.

13. The method according to claim 11, wherein said biotherapeutic agent is a catalytic antibody.

14. The method according to claim 1 wherein the deimmunised antibody is a humanised antibody.

15. The method according to any one of claims 1, 2, 3, or 14 wherein said proteinaceous or non-proteinaceous molecule kills tumour cells.

16. The method according to any one of claims 1, 2, 3 or 14 wherein said mammal is a human.

\* \* \* \* \*